United States Patent
Goto

(10) Patent No.: US 8,958,616 B2
(45) Date of Patent: Feb. 17, 2015

(54) IMAGE PROCESSING DEVICE AND IMAGE PROCESSING METHOD

(75) Inventor: Yoshihiro Goto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 78 days.

(21) Appl. No.: 13/988,451

(22) PCT Filed: Nov. 24, 2011

(86) PCT No.: PCT/JP2011/076975
§ 371 (c)(1),
(2), (4) Date: May 20, 2013

(87) PCT Pub. No.: WO2012/073769
PCT Pub. Date: Jun. 7, 2012

(65) Prior Publication Data
US 2013/0243288 A1    Sep. 19, 2013

(30) Foreign Application Priority Data

Nov. 29, 2010   (JP) ................................. 2010-264518
Sep. 5, 2011    (JP) ................................. 2011-192501

(51) Int. Cl.
  G06K 9/00   (2006.01)
  G06K 9/62   (2006.01)
  G06T 5/00   (2006.01)
  A61B 5/00   (2006.01)
  G06F 19/00  (2011.01)

(52) U.S. Cl.
  CPC ............. *G06K 9/6204* (2013.01); *G06T 5/009* (2013.01); *G06T 2207/10081* (2013.01); *G06T 2207/10088* (2013.01); *G06T 2207/10132* (2013.01); *G06F 19/321* (2013.01)
  USPC ............................................ 382/128; 600/300

(58) Field of Classification Search
  None
  See application file for complete search history.

(56) References Cited

U.S. PATENT DOCUMENTS

2007/0269089 A1* 11/2007 Sakaida ................... 382/128
2012/0237098 A1*  9/2012 Rognin et al. ............. 382/131

FOREIGN PATENT DOCUMENTS

| JP | 9-299349       | 11/1997 |              |
|----|----------------|---------|--------------|
| JP | 09-299349      | * 11/1997 | ............ A61B 5/055 |
| JP | 2001-76141     | 3/2001  |              |
| JP | 2007-307205    | 11/2007 |              |
| WO | WO 2010/013379 | 2/2010  |              |

OTHER PUBLICATIONS

International Search Report in PCT/JP2011/076975.

* cited by examiner

*Primary Examiner* — Amara Abdi
(74) *Attorney, Agent, or Firm* — Cooper & Dunham LLP

(57) ABSTRACT

In order to provide an image processing device which can select and apply an optimal processing algorithm among a plurality of processing algorithms depending on a part of a processing target image and a processing purpose, reference characteristic curve data is calculated in which pixel values are integrated centered on a centroid of a region of interest for a reference image, and the reference characteristic curve data and a processing algorithm according to a processing purpose are stored in advance in an algorithm table 2 in correlation with each other at least for each part.

14 Claims, 26 Drawing Sheets

FIG.2

2 ALGORITHM TABLE

| algoN | | | |
|---|---|---|---|
| A1 | N1 | P1 | DATA D1 |
| A2 | N2 | P2 | DATA D2 |
| A3 | N3 | P3 | DATA D3 |
| A4 | N4 | P4 | DATA D4 |

FIG.5
(a)
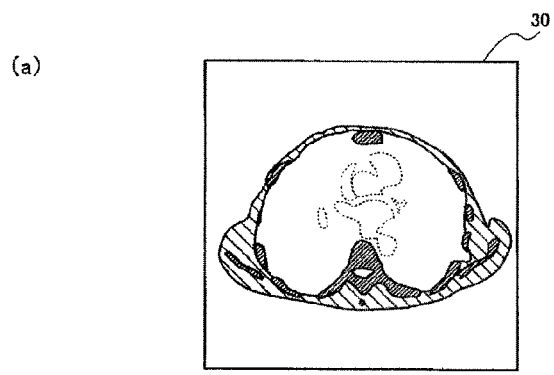
(b)
INTEGRATED VALUE IN RADIUS
VECTOR DIRECTION
$\begin{pmatrix} \text{ADDITION OF} \\ \text{BINARY} \\ \text{IMAGE} \end{pmatrix}$
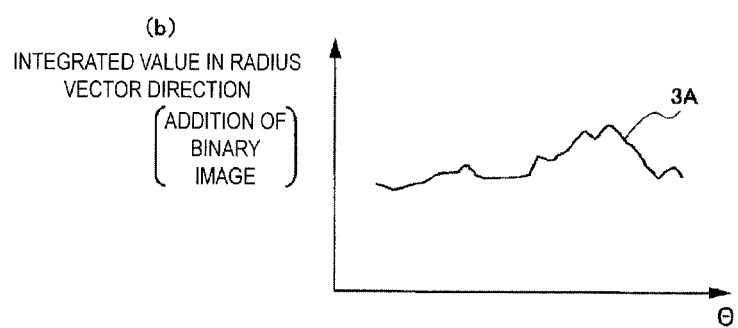
(c)
INTEGRATED VALUE IN ONE
ROUND
$\begin{pmatrix} \text{ADDITION OF} \\ \text{BINARY} \\ \text{IMAGE} \end{pmatrix}$
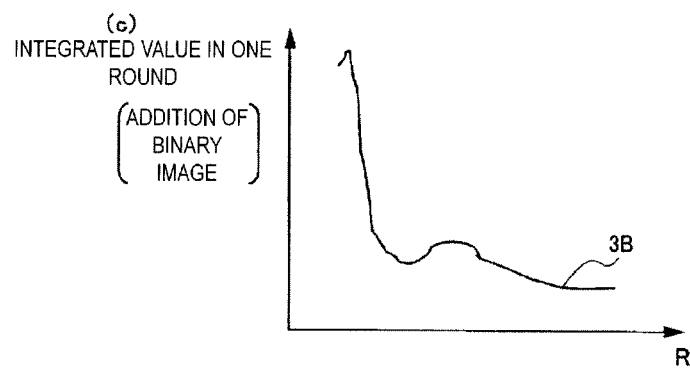

FIG.6
(a)
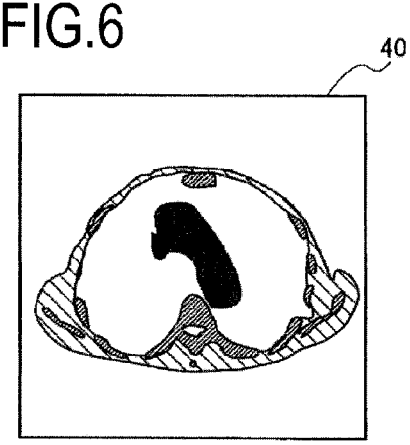
(b)
INTEGRATED VALUE IN RADIUS
VECTOR DIRECTION
$$\begin{pmatrix} \text{ADDITION OF} \\ \text{BINARY} \\ \text{IMAGE} \end{pmatrix}$$
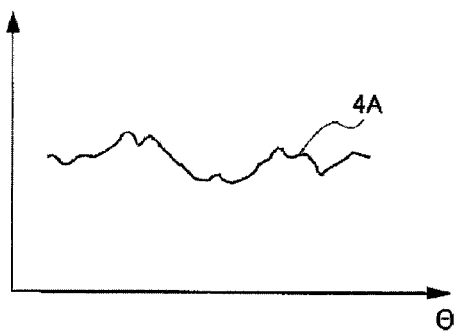
(c)
INTEGRATED VALUE IN ONE
ROUND
$$\begin{pmatrix} \text{ADDITION OF} \\ \text{BINARY} \\ \text{IMAGE} \end{pmatrix}$$
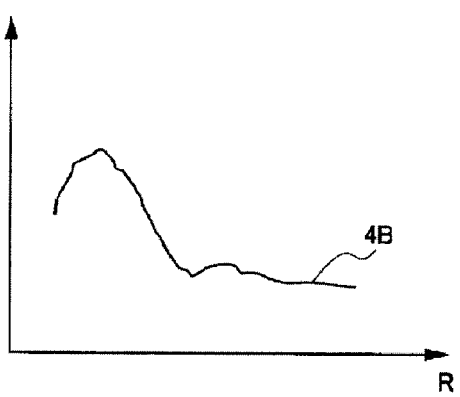

FIG.7
(a)
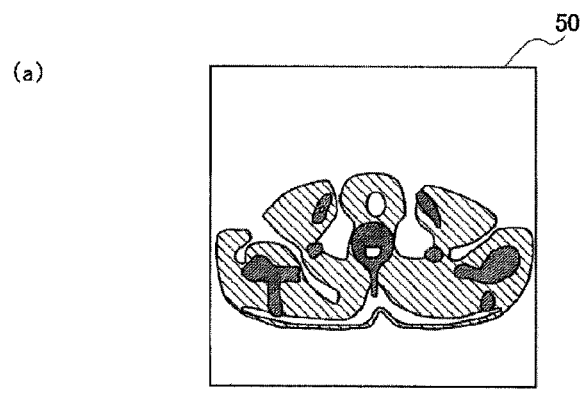
(b)
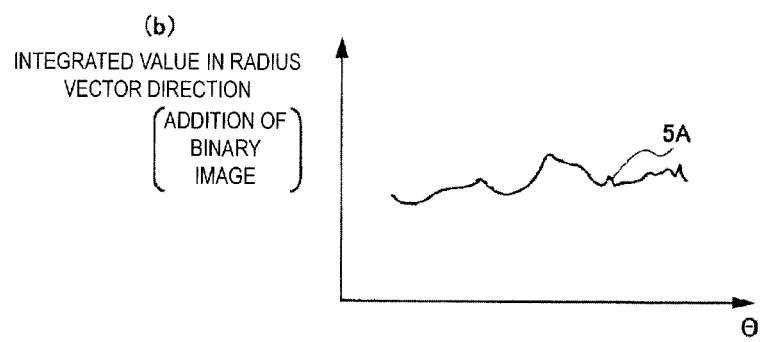
(c)
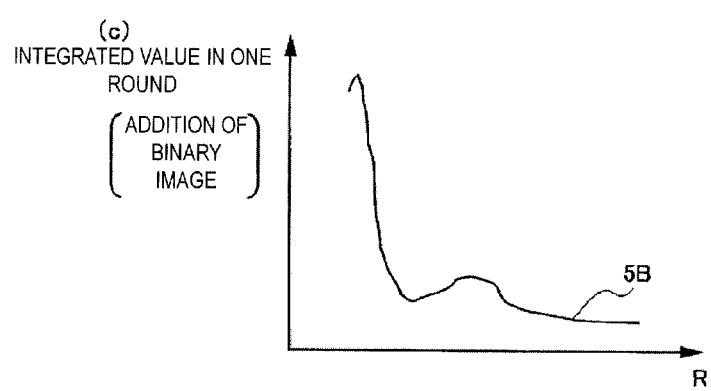

FIG.8
(a)
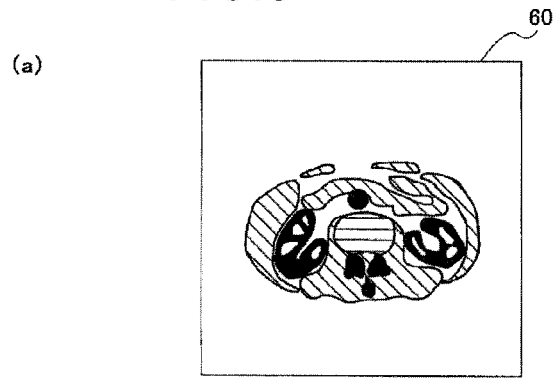
(b)
INTEGRATED VALUE IN REDIUS
VECTOR DIRECTION
$\begin{pmatrix} \text{ADDITION OF} \\ \text{BINARY} \\ \text{IMAGE} \end{pmatrix}$
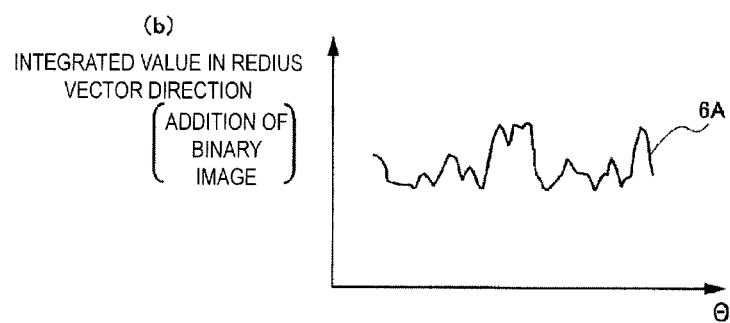
(c)
INTEGRATED VALUE IN ONE
ROUND
$\begin{pmatrix} \text{ADDITION OF} \\ \text{BINARY} \\ \text{IMAGE} \end{pmatrix}$
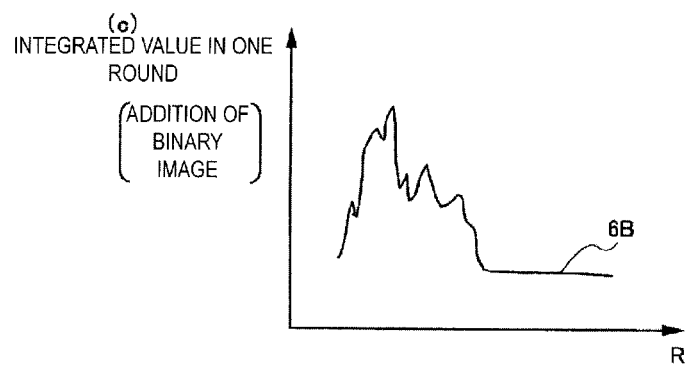

FIG.11
(a)
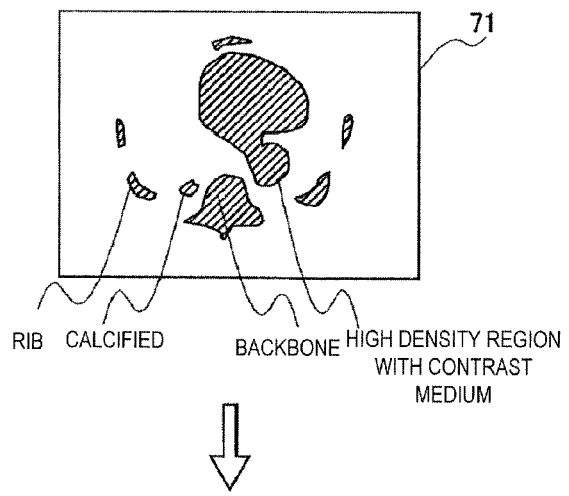
RIB  CALCIFIED  BACKBONE  HIGH DENSITY REGION WITH CONTRAST MEDIUM
(b)
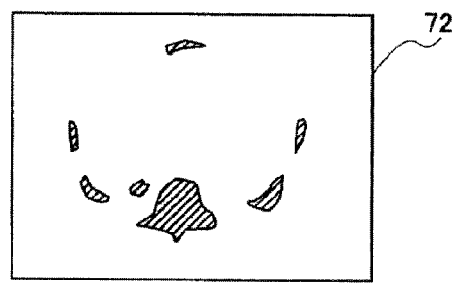
(c)
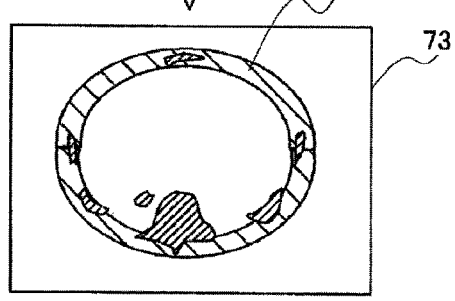

FIG.12
(a) 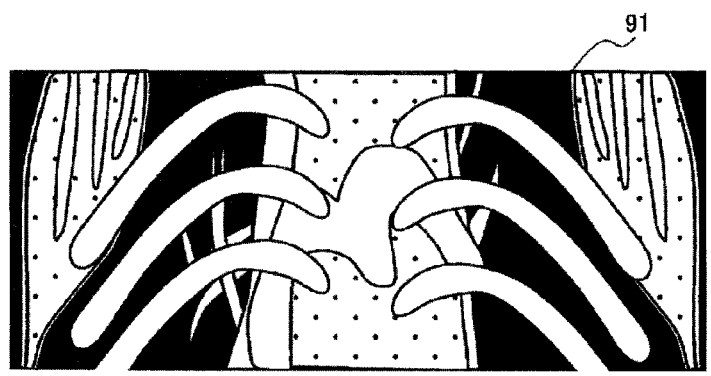
(b) 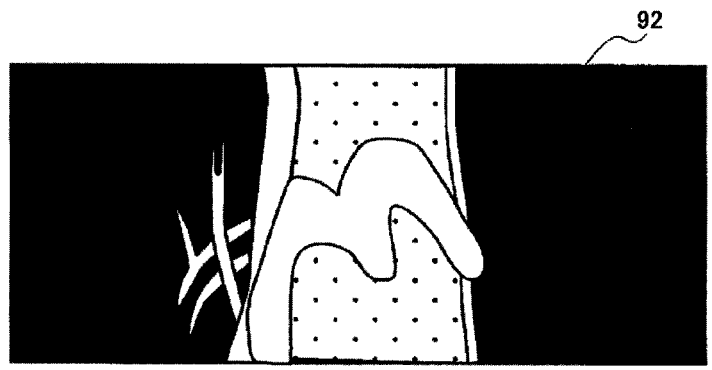

FIG.16
(a) 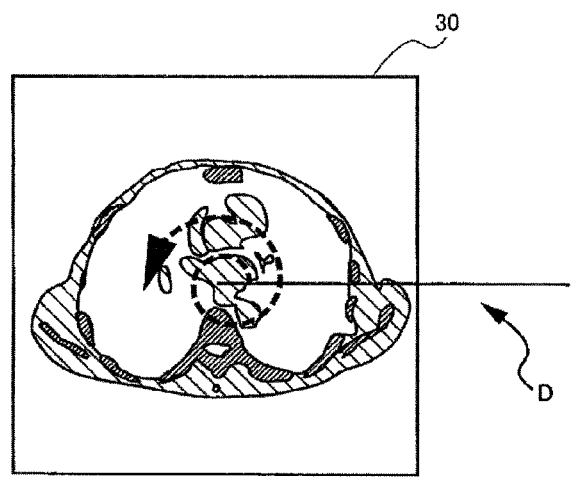
(b) 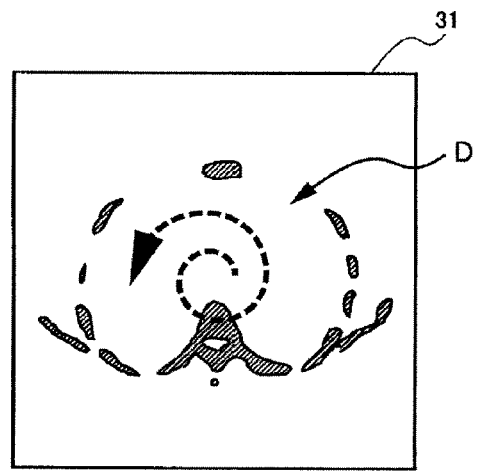

FIG.18

200 ALGORITHM TABLE

| ALGORITHM | ANATOMICAL FEATURE | PART | SUBDIVIDED PART | KIND OF IMAGE | REFERENCE CHARACTERISTIC CURVE |
|---|---|---|---|---|---|
| A 2 1 | C 2 1 | LEG | — | — | — |
| A 2 2 | C 2 2 | ABDOMEN | — | — | — |
| A 2 3 | C 2 3 | NECK | — | — | — |
| ... | | | | | |
| A n_0 1 | C n | CHEST | UPPER PART | WITH CONTRAST MEDIUM | DATA D21 |
| A n_0 2 | | | | WITHOUT CONTRAST MEDIUM | DATA D22 |
| A n_0 3 | | | LOWER PART | WITH CONTRAST MEDIUM | DATA D23 |
| A n_0 4 | | | | WITHOUT CONTRAST MEDIUM | DATA D24 |
| An+1_01 | C n+1 | HEAD | TOP | — | DATA D25 |
| An+1_02 | | | VISINITY OF EYEBALL | — | DATA D26 |
| ... | | | | | |
| A m | — | — | — | — | DATA Dm |
| Am+1 | — | — | — | — | DATA Dm+1 |
| ... | | | | | | ately described image processing device that can solve the above problems.

IMAGE PROCESSING DEVICE AND IMAGE PROCESSING METHOD

TECHNICAL FIELD

The present invention relates to an image processing on a medical image such as a CT image, an MR image, or a US image.

BACKGROUND ART

In the related art, a diagnosis has been performed using a medical image such as a Computed Tomography (CT) image, a Magnetic Resonance (MR) image, or an Ultrasound (US) image. In addition, various image processing methods for extracting an observation target part or removing an unnecessary region from the medical image so as to create an image suitable for the diagnosis have been proposed. Further, a computer aided diagnosis device called Computer Aided Diagnosis (CAD) for detecting abnormal shadows from a medical image has been developed. As above, a plurality of processing algorithms corresponding to various processing purposes for a medical image have been developed.

However, a medical image shows different features depending on a scanning part or the kind of examination. For this reason, to perform a processing in a different process depending on parts achieves good efficiency even in the same processing purpose. For example, when an abnormal shadow is detected from a medical image, a different abnormal shadow detection algorithm is applied depending on a scanning part or diagnosis content. For example, the head and the abdomen employ different abnormal shadow detection algorithms. As a device for selecting an abnormal shadow detection algorithm appropriate for a medical image, for example, an abnormal shadow detection device disclosed in PTL 1 has been proposed.

PTL 1 discloses an abnormal shadow detection device which stores an abnormal shadow detection algorithm for each part of an object, and, when an abnormal shadow is detected from a medical image, creates a set of tomographic images of the anatomically same part which is scanned at different dates and times, obtains a difference between the tomographic images of each set, identifies an object part of the tomographic image, and selects and applies an abnormal shadow detection algorithm for and to the identified part.

CITATION LIST

Patent Literature

PTL 1: Japanese Patent No. 4401121

SUMMARY OF INVENTION

Technical Problem

However, in the above-described PTL 1, when a scanning part is identified from a medical image, the scanning part is determined from continuity of a target image (tomographic image) with previous and subsequent tomographic images, a distribution form of pixels in a specific pixel value range, or the like. For example, it is determined whether or not a scanning part is the head based on whether or not an elliptical region with a high CT value corresponding to the skull is present in an image. In addition, it is determined whether or not a scanning part is the neck based on whether or not the part is a region which is continued from head slices. Further, it is determined whether or not a scanning part is the chest based on whether or not there is a hollow closed region of which a CT value is −900 or less (the specification, paragraphs [0031] to [0036] of PTL 1).

In addition, in a case where the kind of image (the kind of examination, the kind of scanning method, with or without a contrast medium, and the like) is different even if a scanning part is the same and a processing purpose is the same, there is a case where a processing time is reduced by employing a different processing algorithm. For example, since an image obtained without using a contrast medium and an image obtained using the contrast medium show different features, a processing may be performed at high speed by employing a different processing algorithm.

The present invention has been made in consideration of the above-described problems, and an object thereof is to provide an image processing device capable of selecting and applying the optimal processing algorithm according to a part of a processing target image and a processing purpose among a plurality of processing algorithms.

Solution to Problem

In order to achieve the above-described object, a first invention relates to an image processing device which applies a predetermined processing algorithm to a medical image so as to perform an image processing, including a storage unit that calculates reference characteristic curve data in which pixel values are computed centered on any point of a region of interest for a reference image, and stores the reference characteristic curve data and a part in correlation with each other in advance; a calculation unit that calculates target characteristic curve data in which pixel values are computed centered on any point of a region of interest for a processing target image; a comparison unit that compares the target characteristic curve data calculated by the calculation unit with the reference characteristic curve data stored in the storage unit; a selection unit that selects a processing algorithm stored in correlation with reference characteristic curve data having high correlation with the target characteristic curve data from the storage unit on the basis of a result of the comparison by the comparison unit; and an image processing unit that performs an image processing to which a processing algorithm corresponding to the part selected by the selection unit is applied.

A second invention relates to an image processing method of applying a predetermined processing algorithm to a medical image so as to perform an image processing, including a storage step of calculating reference characteristic curve data in which pixel values are computed centered on any point of a region of interest for a reference image, and storing the reference characteristic curve data and a part in correlation with each other in advance; a calculation step of calculating target characteristic curve data in which pixel values are computed centered on any point of a region of interest for a processing target image; a comparison step of comparing the target characteristic curve data calculated in the calculation step with the reference characteristic curve data stored in the storage step; a selection step of selecting a processing algorithm stored in correlation with reference characteristic curve data having high correlation with the target characteristic curve data from the storage step on the basis of a result of the comparison in the comparison step; and an image processing step of performing an image processing to which a processing algorithm corresponding to the part selected in the selection step is applied.

Advantageous Effects of Invention

According to the present invention, it is possible to provide an image processing device and the like capable of selecting and applying the optimal processing algorithm according to a part of a processing target image and a processing purpose among a plurality of processing algorithms.

BRIEF DESCRIPTION OF DRAWINGS

FIG. 2 is a diagram illustrating an example of the algorithm table 2 stored in the image processing device 100 related to the present invention.

FIG. 5(a) is a diagram illustrating an example of the chest tomographic image (without contrast medium) 30, FIG. 5(b) is a diagram illustrating an example of the on-radius vector pixel value data 3A which is extracted from a binary image of the chest tomographic image (without contrast medium) 30, and FIG. 5(c) is a diagram illustrating an example of the on-circumference pixel value data 3B which is extracted from a binary image of the chest tomographic image (without contrast medium) 30.

FIG. 6(a) is a diagram illustrating an example of the chest tomographic image (with contrast medium) 40, FIG. 6(b) is a diagram illustrating an example of the on-radius vector pixel value data 4A which is extracted from a binary image of the chest tomographic image (with contrast medium) 40, and FIG. 6(c) is a diagram illustrating an example of the on-circumference pixel value data 4B which is extracted from a binary image of the chest tomographic image (without contrast medium) 40.

FIG. 7(a) is a diagram illustrating an example of the upper chest end tomographic image (without contrast medium) 50, FIG. 7(b) is a diagram illustrating an example of the on-radius vector pixel value data 5A which is extracted from a binary image of the upper chest end tomographic image (without contrast medium) 50, and FIG. 7(c) is a diagram illustrating an example of the on-circumference pixel value data 5B which is extracted from a binary image of the upper chest end tomographic image (without contrast medium) 50.

FIG. 8(a) is a diagram illustrating an example of the abdomen tomographic image (with contrast medium) 60, FIG. 8(b) is a diagram illustrating an example of the on-radius vector pixel value data 6A which is extracted from a binary image of the abdomen tomographic image (with contrast medium) 60, and FIG. 8(c) is a diagram illustrating an example of the on-circumference pixel value data 6B which is extracted from a binary image of the abdomen tomographic image (with contrast medium) 60.

FIG. 11 is a diagram illustrating the rib extraction algorithm of the chest image with contrast medium.

FIG. 12(a) is a diagram illustrating a chest MIP image 91 before a rib removal processing is performed, and FIG. 12(b) is a diagram illustrating a chest MIP image 92 after the rib removal processing is performed.

FIG. 16 is a diagram illustrating another example (spiral shape) of the characteristic curve data extraction.

FIG. 18 is a diagram illustrating an example of the algorithm table 200 of a second embodiment.

DESCRIPTION OF EMBODIMENTS

Hereinafter, embodiments of the present invention will be described in detail with reference to the drawings.

First Embodiment

First, the configuration of an image processing system 1 to which an image processing apparatus 100 of the present invention is applied will be described with reference to FIG. 1.

Figure 1:
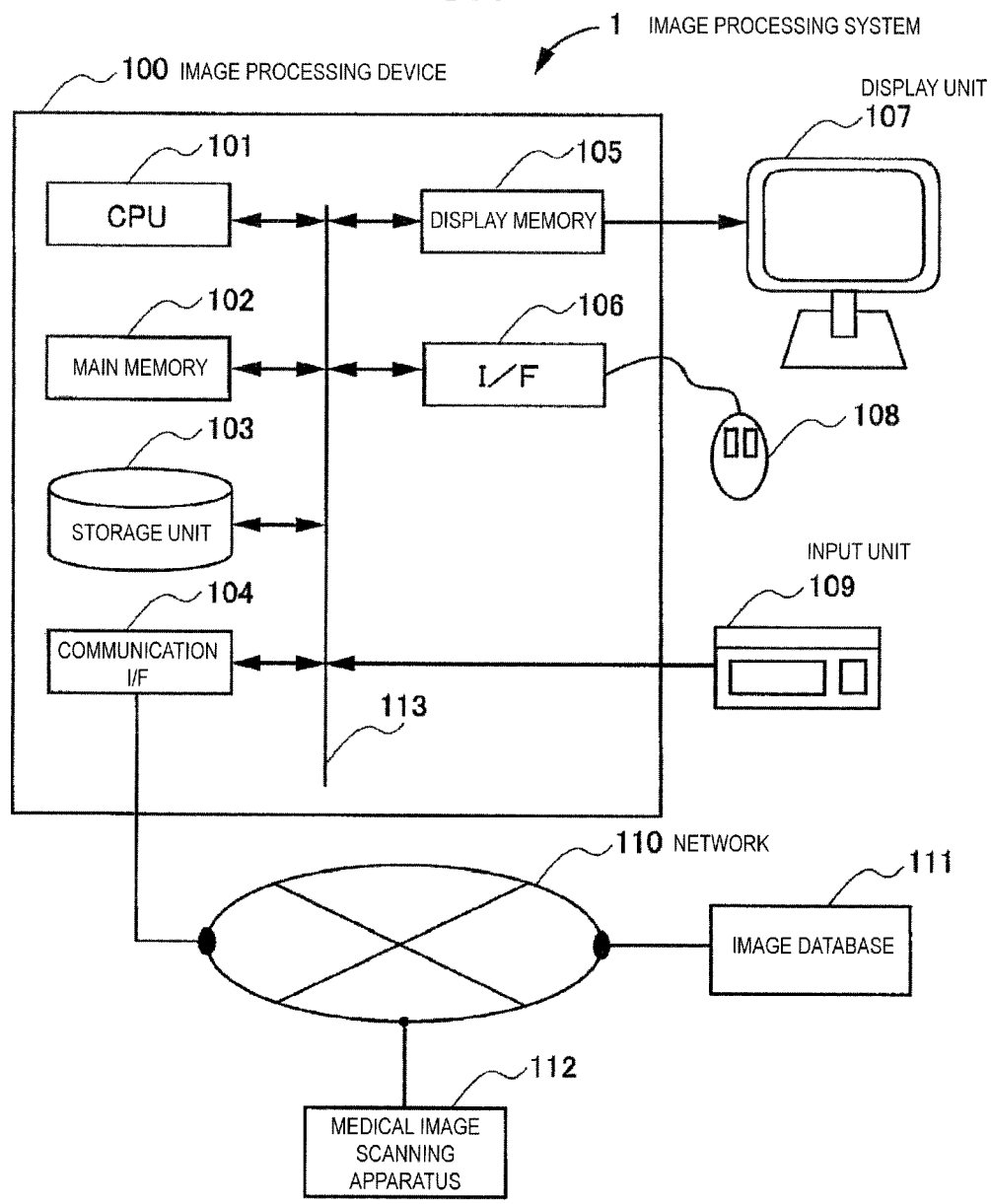
FIG. 1 is a diagram illustrating an overall configuration of an image processing device 100.

As shown in FIG. 1, the image processing system 1 includes the image processing device 100 having a display unit 107 and an input unit 109; an image database 111 connected to the image processing device 100 through a network 110; and a medical image capturing device 112.

The image processing device 100 is a computer which performs processings, such as image generation and image analysis.

As shown in FIG. 1, the image processing device 100 includes a CPU (Central Processing Unit) 101, a main memory 102, a storage unit 103, a communication interface (communication I/F) 104, a display memory 105, and an interface (I/F) 106 with an external unit such as a mouse 108, and the respective units are connected to each other through a bus 113.

The CPU 101 loads a program stored in the main memory 102 or the storage unit 103 to a work memory region on a RAM of the main memory 102 and executes the program and performs driving control of the respective units connected to each other through the bus 113, thereby realizing various kinds of processings performed by the image processing device 100.

Figure 3:
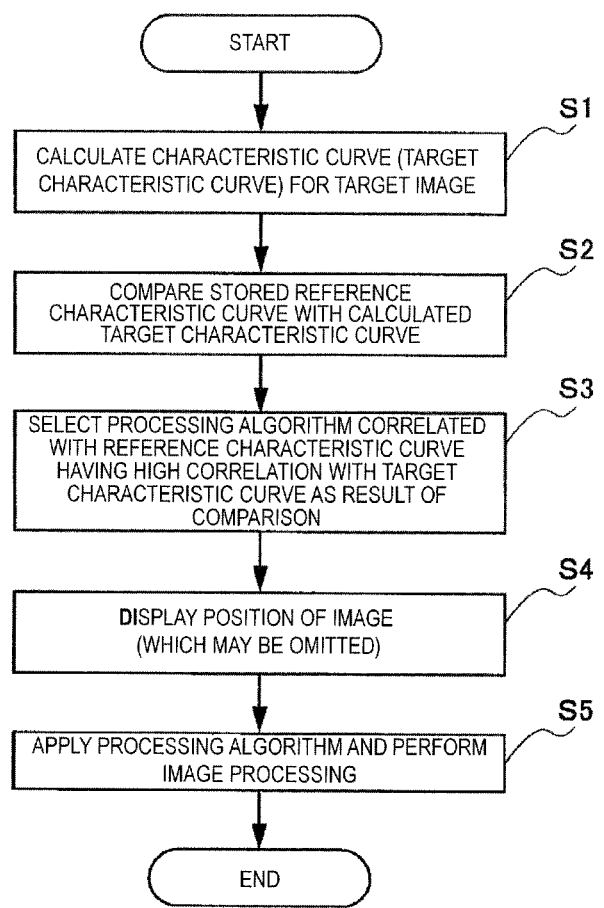
FIG. 3 is a flowchart illustrating a flow of the algorithm selection processing.

In addition, in the first embodiment, when the CPU 101 performs the intended processing on a processing target image, the CPU executes an algorithm selection processing (FIG. 3) described later, so as to select and apply the optimal processing algorithm. The algorithm selection processing will be described later.

The main memory 102 is configured to include a ROM (Read Only Memory), a RAM (Random Access Memory), and the like. The ROM permanently holds a boot program of a computer, a program such as BIOS, data, and the like. In addition, the RAM temporarily holds a program, data, and the like loaded from the ROM, the storage unit 103, and the like, and has a work area used when the CPU 101 performs various kinds of processings.

The storage unit 103 is a storage unit which performs reading and writing of data from and in a HDD (hard disk drive) or other recording media. Programs executed by the CPU 101, data required to execute the programs, an OS (Operating System), and the like are stored in the storage unit 103. As programs, a control program equivalent to an OS and application programs are stored. Each of these program codes is read by the CPU 101 as necessary and moved to the RAM of the main memory 102, thereby being executed as various kinds of means.

In addition, the storage unit 103 stores an algorithm table 2 shown in FIG. 2.

As shown in FIG. 2, in the algorithm table 2, reference characteristic curve data items D1, D2, . . . which are calculated from a reference image and processing algorithms A1, A2, . . . are registered so to be correlated with each other. The reference characteristic curve data items D1, D2, . . . are calculated at least for the respective parts (position numbers P1, P2, . . . ). Preferably, in addition to the parts, the data is calculated for each kind of image (the kind of examination, the kind of scanning method). As the kind of image, for example, there is a presence or absence of a contrast medium. This algorithm table 2 is prepared in plurality according to processing purposes.

The reference characteristic curve data items D1, D2, . . . are data items which are used as a reference of comparison with target characteristic curve data items in the algorithm selection processing described later.

In addition, reference characteristic curve data items D1, D2, . . . are characteristic curves in which a pixel value distribution of a tomographic image is computed centered on a centroid of a region of interest.

Specifically, the following is calculated as the reference characteristic curve data items.

Figure 4:
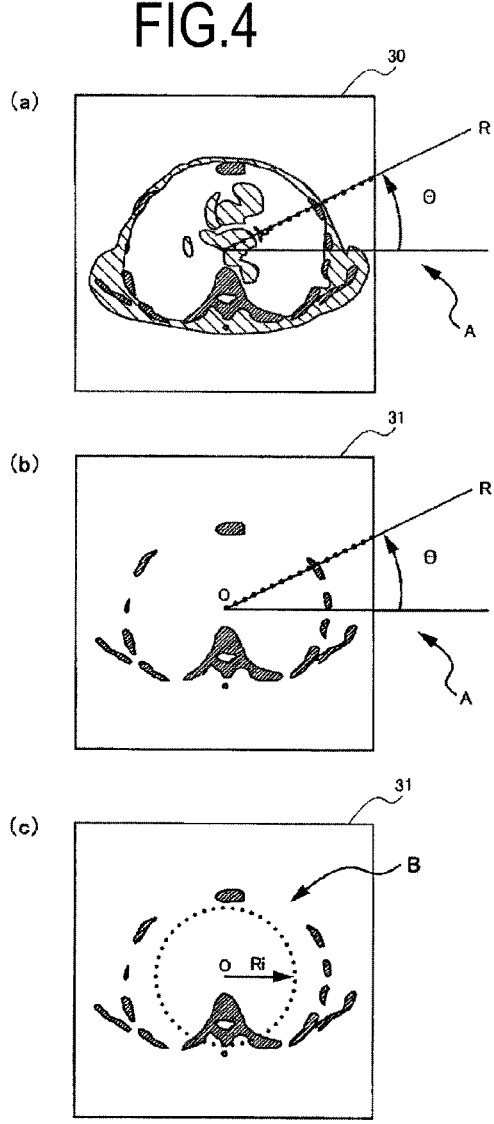
FIG. 4(a) is a diagram illustrating that on-radius vector pixel value data is acquired from a CT image.
FIG. 4(b) is a diagram illustrating that on-radius vector pixel value data is acquired from a binary image.
FIG. 4(c) is a diagram illustrating on-circumference pixel value data is acquired from a binary image.

(1) On-radius vector pixel value data in which pixel values of respective points on a radius vector A which rotates centered on a centroid of a region of interest are integrated for each rotation angle $\theta$ (refer to FIGS. 4(a) and 4(b)).

(2) On-circumference pixel value data in which pixel values of respective points on a circumference B centered on a centroid of a region of interest are integrated for each radius Ri (refer to FIG. 4(c)).

(3) On-ellipse pixel value data in which pixel values of respective points on an circumference of an ellipse centered on a centroid of a region of interest are integrated for each diameter Re of the ellipse (either the minor axis or the major axis) (not shown).

(4) On-radius vector pixel value data in which pixel values of respective points on a radius vector A which rotates centered on a centroid of a region of interest are multiplied by, for example, a weighting factor corresponding to a distance from the centroid so as to be added with weighting for each rotation angle $\theta$.

(5) On-circumference pixel value data in which pixel values of respective points on a circumference B centered on a centroid of a region of interest are multiplied by, for example, a weighting factor corresponding to a rotation angle of the radius vector A so as to be added with weighting for each radius Ri.

In addition, the reference characteristic curve data of a single representative cross-section may be calculated for each part such as the head, the neck, the chest, the abdomen, the lumbar region, or the leg, or the reference characteristic curve data of a plurality of cross-sections may be calculated for each part. When the reference characteristic curve data of a plurality of cross-sections for each part is calculated and is registered in the algorithm table 2, a comparison with not only a target cross-section but also previous and subsequent cross-sections can be performed upon comparison with target characteristic curve data, and thus it is possible to obtain a more accurate comparison result.

In FIG. 2, A1, A2, A3, A4, . . . are identification numbers of algorithms, N1, N2, N3, N4, are the number of sampling points of the reference characteristic curve data items D1, D2, D3, D4, . . . , P1, P2, P3, P4, . . . are numbers indicating anatomical positions of images which are bases of the reference characteristic curve data items D1, D2, D3, and D1, D2, D3, D4, . . . are reference characteristic curve data items.

The number of sampling points of the reference characteristic curve data items D1, D2, D3, D4, . . . are used for normalization. In other words, if the number of sampling points of reference characteristic curve data and target characteristic curve data is normalized so as to be the same, an accurate comparison can be performed regardless of a physique difference between objects.

Each processing algorithm registered in the algorithm table 2 is stored in the storage unit 103.

The communication I/F 104 has a communication control unit, a communication port, and the like, and mediates communication between the image processing device 100 and the network 110. In addition, the communication I/F 104 performs communication control with the image database 111, other computers, or the medical image capturing device 112, such as an X-ray CT device or an MRI device, through the network 110.

The I/F 106 is a port for connection with a peripheral unit and performs transmission and reception of data with the peripheral unit. For example, a pointing device, such as the mouse 108 or a stylus pen, may be connected through the I/F 106.

The display memory 105 is a buffer which temporarily accumulates the display data input from the CPU 101. The accumulated display data is output to the display unit 107 at a predetermined timing.

The display unit 107 is formed by a liquid crystal panel, a display unit such as a CRT monitor, and a logic circuit which cooperates with the display unit to execute a display processing, and is connected to the CPU 101 through the display memory 105. The display unit 107 displays the display data accumulated in the display memory 105 under control of the CPU 101.

The input unit 109 is an input unit, such as a keyboard, for example, and outputs to the CPU 101a variety of instructions or information input by the operator. The operator operates the image processing device 100 interactively using the display unit 107, the input unit 109, and an external unit such as the mouse 108.

In addition, the display unit 107 and the input unit 109 may be integrally formed such as, for example, a touch panel display. In this case, a keyboard array of the input unit 109 is displayed in the touch panel display.

The network 110 includes various communication networks, such as a LAN (Local Area Network), a WAN (Wide Area Network), an intranet, and the Internet, and mediates communication connection between the image database 111, a server, or other information devices and the image processing device 100.

The image database 111 accumulates and stores the image data scanned by the medical image capturing device 112. Although the image processing system 1 shown in FIG. 1 has a configuration in which the image database 111 is connected to the image processing device 100 through the network 110, the image database 111 may be provided, for example, in the storage unit 103 of the image processing device 100.

Next, an operation of the image processing device 100 related to the first embodiment will be described with reference to FIGS. 3 to 17.

The CPU 101 of the image processing device 100 reads from the main memory 102 a program and data regarding the algorithm selection processing shown in FIG. 2 and executes the processing on the basis of the program and data.

In addition, it is assumed that the reference characteristic curve data items D1, D2, D3, D4, . . . for a reference image are calculated and are registered in the algorithm table 2 of the storage unit 103 when execution of the following processing starts, as shown in FIG. 2. In addition, the processing algorithms A1, A2, A3, A4, . . . which are to be applied for each part and kind of image (for example, presence or absence of a contrast medium, or the like) are registered in correlation with the reference characteristic curve data items D1, D2, D3, D4, . . . .

In addition, it is assumed that data of a computation target image (tomographic image) is received from the image database 111 or the like through the network 110 and the communication I/F 104 and is stored in the storage unit 103 of the image processing device 100.

The image is an image scanned by an X-ray CT device, an MRI device, an ultrasonic device, or the like. Although a two-dimensional axial CT image is used in the following example, a coronal image or a sagittal image may be used.

The CPU 101 of the image processing device 100 first acquires an image (CT image) which is a processing target, and obtains characteristic curve data from the acquired image (step S1). Hereinafter, the characteristic curve data for the processing target image is referred to as target characteristic curve data.

Here, calculation of the characteristic curve data will be described.

In the first embodiment, a characteristic curve (reference characteristic curve data and target characteristic curve data) is obtained by integrating a pixel value distribution of an image, centered on a centroid of a region of interest.

In addition, although, in the following, a description will be made of an example in which a region of interest is set to an object region, and a center of the radius vector A or the circumference B is set to a centroid of the object region, a specific organ may be set as a region of interest such as a backbone region being set as the region of interest.

In a case where on-radius vector pixel value data is acquired as the characteristic curve, as shown in FIG. 4(a), the CPU 101 sets the radius vector A which rotates centered on a centroid of a region of interest on an image 30, and integrates pixel values (CT values in FIG. 4(a)) of the respective points on the radius vector A for each rotation angle θ. Then, an integrated value (on-radius vector pixel value data) of the pixel values for the rotation angle θ is obtained as shown in FIGS. 5(b), 6(b), 7(b), 8(b), and the like. FIGS. 5(b), 6(b), 7(b) and 8(b) show examples of the on-radius vector pixel value data items 3A, 4A, 5A and 6A in which the transverse axis is expressed by θ, and the longitudinal axis is expressed by an integrated value. Any width of the rotation angle θ may be used, and, for example, π/180[rad] may be used.

In addition, as shown in FIG. 4(b), a target pixel may be binarized using a predetermined threshold value, the respective pixel values ("1" or "0") on the radius vector in the binarized tomographic image (a binary image 31) may be integrated so as to calculate on-radius vector pixel value data. If the on-radius vector pixel value data is calculated from the binary image 31, addition processing is easily performed, and thus the calculation can be performed at high speed.

In addition, in a case where on-circumference pixel value data is acquired as the characteristic curve data, as shown in FIG. 4(c), the CPU 101 sets the circumference B which is centered on a centroid of a region of interest on the image 30 or the binary image 31, and integrates pixel values of the respective points on the circumference B for each radius Ri. Then, an integrated value (on-circumference pixel value data) of the pixel values for the radius Ri is obtained as shown in FIGS. 5(c), 6(c), 7(c), 8(c), and the like. FIGS. 5(c), 6(c), 7(c) and 8(c) show examples of the on-circumference pixel value data items 3B, 4B, 5B and 6B in which the transverse axis is expressed by Ri, and the longitudinal axis is expressed by an integrated value. Any step size of the radius Ri may be used, and, for example, one pixel may be used. FIG. 4(c) shows an example in which the respective values ("1" or "0") of the binary image 31 are integrated; however, on-circumference pixel value data may be acquired from a CT image (not shown).

In addition, the circle B of the above-described on-circumference pixel value data may be set to an ellipse, and on-ellipse pixel value data may be acquired as the characteristic curve data. In this case, the CPU 101 integrates pixel values of the respective points on a circumference of an ellipse for each diameter (either the minor axis or the major axis) Re of the ellipse, and generates on-ellipse pixel value data in which the transverse axis is expressed by Re, and the longitudinal axis is expressed by an integrated value. Also for the on-ellipse pixel value data, in the same manner as the on-radius vector pixel value data and the on-circumference pixel value data, either a CT value or a binary value may be used as a computation target, and the characteristic curve data may be acquired (not shown).

In addition, in a case where CT values are integrated, the CPU 101 may add the CT values by being multiplied by a weighting factor depending on the CT value. For example, if each pixel value is multiplied by a reciprocal of the maximum CT value as a weighting factor for all pixels, an additional value can be made to be small, and thus it is possible to prevent an overflow.

In addition, in order to correspond to a physique of an object, a length between a centroid (a center of the radius vector A) and a body surface of the object is preferably normalized, that is, the number of sampling points up to the body surface is normalized. Alternatively, in a case where the number of sampling points is different, an interpolation computation is performed when correlation with a reference characteristic curve is computed in step S2 (comparison processing) described later, thereby making the number of sampling points equal.

By normalizing the characteristic curve data in the above-described way, it is possible to perform an accurate comparison even if an object image is different in a physique from a reference tomographic image which is a base of reference characteristic curve data.

FIGS. 5 to 8 are diagrams illustrating examples of the characteristic curve data items which are calculated for tomographic images of different parts.

FIG. 5(a) is a diagram illustrating a contrast medium absent chest tomographic image 30, FIG. 5(b) is a diagram illustrating on-radius vector pixel value data 3A which is extracted from a binary image of the contrast medium absent chest tomographic image 30 of FIG. 5(a), and FIG. 5(c) is an example of the on-circumference pixel value data 3B which is extracted from a binary image of the contrast medium absent chest tomographic image 30 of FIG. 5(a).

In addition, FIG. 6(a) is a diagram illustrating a contrast medium present chest tomographic image 40, FIG. 6(b) is a diagram illustrating on-radius vector pixel value data 4A which is extracted from a binary image of the contrast medium present chest tomographic image 40 of FIG. 6(a), and FIG. 6(c) is a diagram illustrating an example of on-circumference pixel value data 4B which is extracted from a binary image of the contrast medium present chest tomographic image 40 of FIG. 6(a).

Further, FIG. 7(a) is a diagram illustrating a contrast medium absent upper chest end tomographic image 50, FIG. 7(b) is a diagram illustrating on-radius vector pixel value data 5A which is extracted from a binary image of the contrast medium absent upper chest end tomographic image 50 of FIG. 7(a), and FIG. 7(c) is a diagram illustrating on-circumference pixel value data 5B which is extracted from a binary image of the contrast medium absent upper chest end tomographic image 50 of FIG. 7(a).

In addition, FIG. 8(a) is a diagram illustrating an example of a contrast medium present abdomen tomographic image 60, FIG. 8(b) is a diagram illustrating on-radius vector pixel value data 6A which is extracted from a binary image of the contrast medium present abdomen tomographic image 60 of FIG. 8(a), and FIG. 8(c) is a diagram illustrating on-circumference pixel value data 6B which is extracted from a binary image of the contrast medium present abdomen tomographic image 60 of FIG. 8(a).

As shown in FIGS. 5 to 8, the on-radius vector pixel value data items 3A to 6A and the on-circumference pixel value data items 3B to 6B represent different curves depending on the parts and the presence or absence of the contrast medium. Although not shown, on-ellipse pixel value data also represents different curves depending on the parts and the presence or absence of the contrast medium.

In other words, for example, even in the same chest, characteristic curves are different depending on the upper chest (apex area) or the middle chest, and are more greatly different between the chest and the abdomen.

Characteristic curve data of other parts such as the head, the neck, the lumbar region, the leg, and the foot region can be calculated in the same manner.

In step S1, when target characteristic curve data (at least one of the on-radius vector pixel value data, the on-circumference pixel value data, and the on-ellipse pixel value data) is calculated, the CPU 101 then compares each reference characteristic curve data item stored in the storage unit 103 with the target characteristic curve data item calculated in step S1 (step S2).

The comparison processing in step S2 is performed, for example, by calculating the magnitude of correlation between the target characteristic curve data and the reference characteristic curve data.

The magnitude of correlation may be calculated using the Pearson product-moment correlation coefficient represented by the following Equation (1).

[Equation 1]

$$r = \frac{\text{(Covariance of variable } X \text{ and variable } Y\text{)}}{\left(\begin{array}{c}\text{standard deviation of variable } X \times \\ \text{standard deviation of variable } Y\end{array}\right)} \quad (1)$$

$$= \frac{\frac{1}{n-1}\sum_{i=1}^{n}(X_i - \overline{X})(Y_i - \overline{Y})}{\sqrt{\frac{1}{n-1}\sum_{i=1}^{n}(X_i - \overline{X})^2}\sqrt{\frac{1}{n-1}\sum_{i=1}^{n}(Y_i - \overline{Y})^2}}.$$

In addition, for simpler comparison, an inter-curve distance between the characteristic curve data items is calculated, for example, using either one of the following Equations (2) and (3), and the data items with the minimum distance may have the highest correlation.

[Equation 2]

$$\text{Inter-curve distance} = \Sigma(X_i - Y_i)^2 \quad (2)$$

[Equation 3]

$$\text{Inter-curve distance} = \Sigma \text{abs}(X_i - Y_i) \quad (3)$$

In addition, in relation to the comparison between the reference characteristic curve data and the target characteristic curve data, the same kind of characteristic curve data may be compared such as comparison between the on-radius vector pixel value data items (hereinafter, also indicated by A(θ) in some cases), comparison between the on-circumference pixel value data (hereinafter, also indicated by B(R) in some cases), or comparison between the on-ellipse pixel value data (hereinafter, also indicated by C(Re) in some cases), or the different kinds of a plurality of characteristic curve data items may be combined into a single curve (for example, A(θ)+B(R)+C(Re)) and may be compared with each other.

In addition, since the backbone is reflected in both the chest image and the abdomen image and thus is not characteristic, the on-radius vector pixel value data for this region may not be used. Alternatively, a small weighting factor WA may be applied to the on-radius vector pixel value data for this region, and a curve (WA×A(θ)+WB×B(R)+WC×C(Re)) may be compared into which the on-radius vector pixel value data A(θ), the on-circumference pixel value data B(R), and the on-ellipse pixel value data C(Re) are combined.

Next, the CPU 101 selects from the algorithm table 2 a processing algorithm which is correlated with the reference characteristic curve data having high correlation with the target characteristic curve data as a result of the comparison in step S2 (step S3). In other words, a processing algorithm is selected which is correlated with reference characteristic curve data with the greatest product-moment correlation coefficient of the above-described Equation (1) or reference characteristic curve data with the shortest inter-curve distance of the above-described Equations (2) and (3).

In addition, as the result of the comparison in step S2, the CPU 101 acquires a position number (P1, P2, . . . of the algorithm table 2 of FIG. 2) correlated with the reference characteristic curve data having the highest correlation with the target characteristic curve data, and displays a part presentation image 82 which shows a part corresponding to the position number (step S4).

Figure 9:
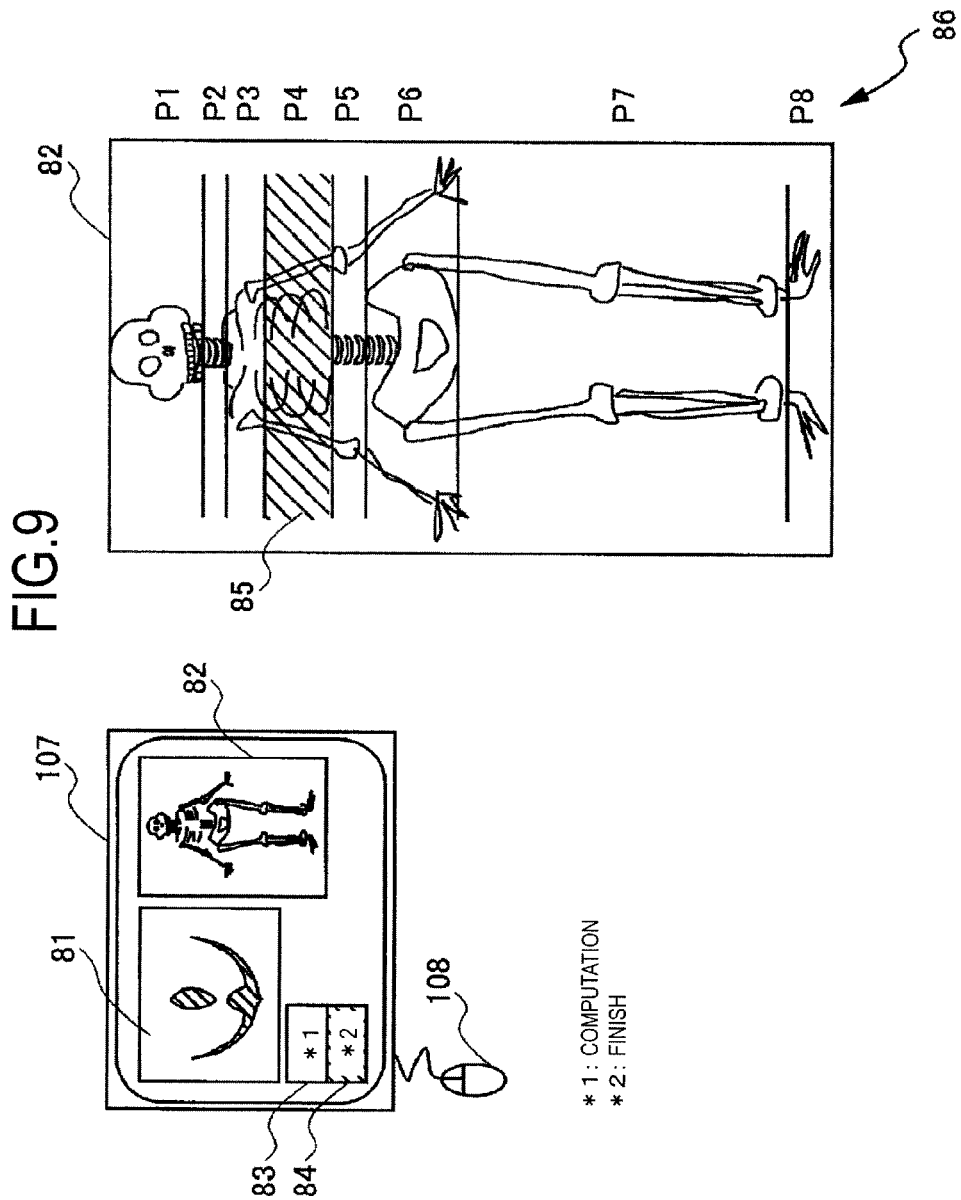
FIG. 9 is a diagram illustrating a part presentation image 82 showing a part of a tomographic image.

An example of the part presentation image 82 is shown in FIG. 9.

As shown in FIG. 9, an image processing operation screen shown on the left side of FIG. 9 is assumed to be displayed on a display screen of the display unit 107. On the image processing operation screen, an image 81 which is a processing target, a "computation" button 83 for instructing the starting of a computation, a "finish" button 84 for instructing the finishing of a processing, the above-described part presentation image 82, and the like are displayed. In addition, although not shown, an operation button or an input column for receiving an operation such as selection of a processing target or selection of a processing purpose may be provided on the image processing operation screen. For example, in a case where an image processing of extracting bones from a tomographic image of the whole body is performed, when a user selects the "whole body" as a processing target, the CPU 101 acquires a series of tomographic images 81 for the whole body from the image database 111. In addition, when "bone extraction" is selected as a processing purpose (not shown), and the "computation" button is operated, the algorithm selection processing of FIG. 3 starts so as to perform the characteristic curve calculation processing in step S1, the characteristic curve comparison processing in step S2, and the algorithm selection processing in step S3. In other words, target characteristic curve data is calculated in order from the first tomographic image, all the reference characteristic curve data items D1, D2, . . . stored in the algorithm table 2 of "bone extraction" which is a processing purpose are compared with the target characteristic curve data, and a processing algorithm correlated with the reference characteristic curve data having the highest correlation is selected. In addition, the CPU 101 obtains a part (for example, the position number "P4") of the tomographic image during the processing on the basis of a result of the comparison processing in step S2, and creates and displays the part presentation image 82 which clearly indicates a corresponding position 85 on a human body image or the like.

In addition, a display processing of the part presentation image 82 in step S4 may be omitted.

Successively, the CPU 101 applies the processing algorithm selected in step S3 to the tomographic image 81 during the processing which is a processing target, so as to perform an image processing (step S5).

If it is determined that the target characteristic curve data of the tomographic image 81 is in a condition of "presence of contrast medium" and has high correlation with the reference characteristic curve data of the "chest" in the comparison processing of step S2 described above, a processing algorithm of FIG. 10 is selected in step S3. In addition, if it is determined that the target characteristic curve data of the tomographic image 81 is in a condition of "absence of contrast medium" and has high correlation with the reference characteristic curve data of the "chest" in the comparison processing of step S2 described above, a processing algorithm of FIG. 13 is selected in step S3 and applied.

Figure 10:
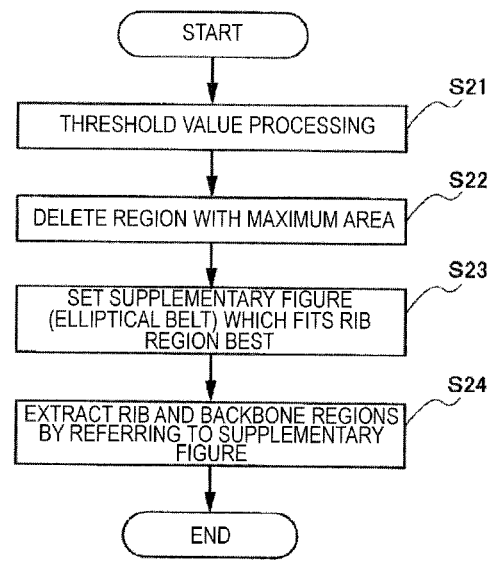
FIG. 10 is a diagram illustrating an example of the rib extraction algorithm applied to a chest image with contrast medium.

In a "contrast medium present" rib extraction algorithm of FIG. 10, first, a threshold value processing is performed on a target image (step S21), and the rib, the calcified region, the backbone, and the high density region where a contrast medium is present, are extracted as shown in an image 71 of FIG. 11(a) after the threshold value processing is performed.

Next, the CPU 101 deletes the region with the maximum area in advance among the extracted regions (step S22). A processing result is as shown in an image 72 of FIG. 11(b). By deleting the region with the maximum area in advance, the region which easily contacts with an elliptical belt set in the next step is removed in advance.

Further, in order to extract only the rib and the backbone, the CPU 101 sets a supplementary FIG. 74 which fits the rib region the best. In the example of FIG. 11, an elliptical belt as shown in FIG. 11(c) is set as the supplementary FIG. 74 from position information of the bones at the left and right ends and position information of the bones at the upper and lower ends (step S23). The CPU 101 extracts the region which contacts with the supplementary figure (elliptical belt) 74 as a bone region (step S24).

By referring to the processing result of the rib extraction processing, a processing of removing the bone region can be performed when a processing on other soft tissues or the like is performed. For example, a specific value such as −100 is overwritten on the bone region of the original CT image by using the extracted bone region information, and thereby an image from which the bone region is removed can be generated. For example, FIG. 12(a) is an MIP (maximum intensity projection) image 91 of the chest; a specific pixel value (for example, −100 or the like) is overwritten on the bone region of the original CT image (presence of contrast medium) by using the bone region information extracted through the rib extraction processing of FIG. 10, this is repeatedly performed on tomographic images of the respective cross-sections, and thereby a series of tomographic images (volume images) from which the bones are removed is generated. In addition, when an MIP image 92 is configured using a series of tomographic images (volume images) from which the bones are removed, the MIP image 92 from which the ribs are removed as shown in FIG. 12(b) is generated.

This is not limited to the MIP image, and may be applied to generation of a three-dimensional image or other processings.

Figure 13:
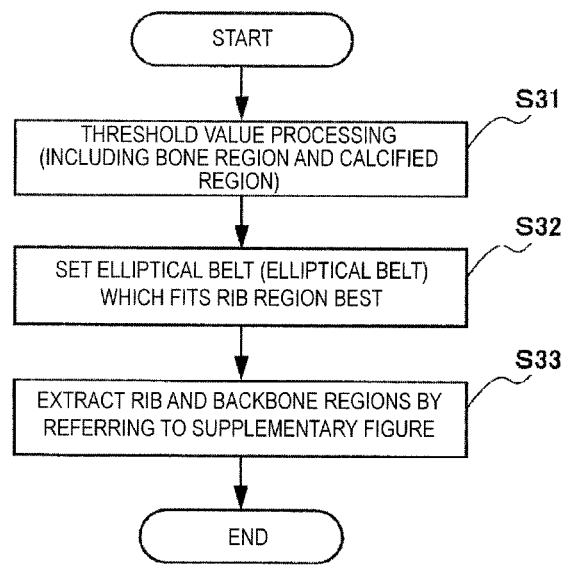
FIG. 13 is a diagram illustrating an example of the rib extraction algorithm applied to a chest image without contrast medium.

In addition, for example, in the "contrast medium absent" rib extraction algorithm of FIG. 13, first, a threshold value processing is performed on a target tomographic image (step S31), and the bone region and the calcified region are extracted as shown in an image 93 of FIG. 14(a) after the threshold value processing is performed.

Next, the CPU 101 sets a supplementary FIG. 74 which fits the rib region the best. The supplementary figure is set in the same manner as in the example of FIG. 7 (step S32). The CPU 101 extracts a region which contacts with the supplementary figure (elliptical belt) 74 as the bone region (step S33).

Figure 14:
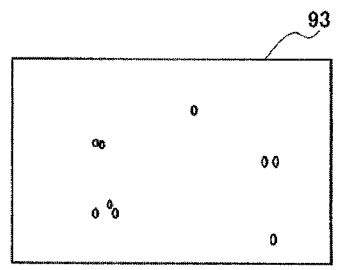
FIG. 14 is a diagram illustrating an MIP image 93 configured by removing a rib from the chest image without contrast medium.

If a specific value such as −100 is overwritten on the bone region of the original CT image by using the extracted bone region information with reference to the processing result of the "contrast medium absent" rib extraction processing, an image from which the bone region is removed can be generated when an image processing on other soft tissues or the like is performed. For example, a specific pixel value (for example, −100 or the like) is overwritten on the bone region of the original CT image (absence of contrast medium) by using the bone region information extracted through the rib extraction processing of FIG. 13, this is repeatedly performed on tomographic images of the respective cross-sections, and thereby a series of tomographic images (volume images) from which the bones are removed is generated. In addition, when an MIP image 93 is configured using a series of tomographic images from which the bones are removed, the MIP image 93 in which the ribs are removed and the calcified region is drawn as shown in FIG. 14 is generated.

In addition to the organ extraction algorithm as shown in FIG. 10 or 13, the processing algorithm may be an organ removal algorithm, an abnormal shadow detection algorithm, an abnormal shadow shape analysis algorithm, an abnormal shadow density analysis algorithm, a noise removal algorithm, and the like, depending on a processing purpose.

These processing algorithms are all correlated with reference characteristic curve data items and are registered in the algorithm table 2 of corresponding processing purposes.

In addition, these processing algorithms are more preferably prepared for each kind of image such as a presence or absence of a contrast medium.

Figure 15:
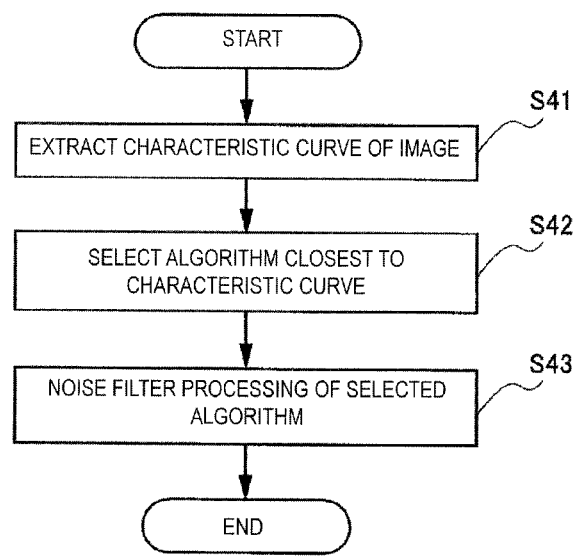
FIG. 15 is a flowchart illustrating a noise removal processing.
Figure 17:
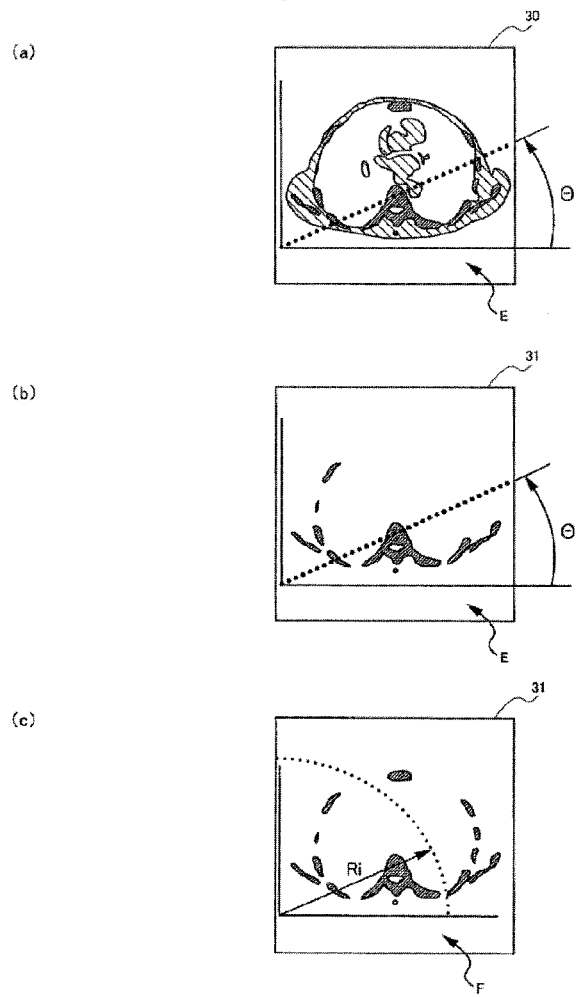
FIG. 17 is a diagram illustrating another example (an example in which a center of a radius vector is set outside an object) of the characteristic curve data extraction.

For example, in a case where "noise removal" is selected as a processing purpose, algorithm selection processing of FIG. 15 is performed referring to the algorithm table 2 in which a plurality of noise removal algorithms are registered for the respective parts.

As shown in FIG. 15, first, the CPU 101 extracts characteristic curve data (at least one of on-radius vector pixel value data, on-circumference pixel value data, and on-ellipse pixel value data) for a processing target image (step S41), and compares the extracted characteristic curve data with the respective reference characteristic curve data items registered in the algorithm table 2 for use in "noise removal", thereby selecting the closest (high correlation) algorithm (step S42). In addition, the selected algorithm is applied to the processing target image (step S43). As a result of the comparison, if it is determined that the image is a chest image, a median filter may be employed as a noise filter, or if it is determined that the image is a leg image, smoothing processing may be performed.

Further, parameters used in each processing algorithm are preferably registered in the algorithm table 2 in correlation with the reference characteristic curve data for each part, for each kind of image or for each processing purpose.

For example, in the rib extraction algorithm shown in FIG. 10 or 13, a threshold value used in the threshold value processing (step S21 and step S31) may be registered in advance depending on a part or a presence or absence of a contrast medium.

In addition, there is a case where a processing algorithm is the same but different parameters are used, and, also in this case, parameters used in correlation with the reference characteristic curve data may be registered in the algorithm table 2 in advance.

As described above, the image processing device 100 of the first embodiment calculates reference characteristic curve data in which pixel values are integrated centered on a centroid of a region of interest with respect to a reference image, and stores in advance the reference characteristic curve data and a processing algorithm according to a processing purpose in the algorithm table 2 in correlation with each other at least for each part. In addition, the CPU 101 calculates target characteristic curve data in which pixel values are integrated centered on a centroid of a region of interest with respect to a processing image, compares the calculated target characteristic curve data with the reference characteristic curve data stored in the algorithm table 2, selects from the algorithm table 2 a processing algorithm correlated with reference characteristic curve data having the highest correlation with the target characteristic curve data on the basis of the comparison result, and performs an image processing to which the selected processing algorithm is applied.

In addition, the reference characteristic curve data and the target characteristic curve data are set as on-radius vector pixel value data in which pixel values on the radius vector A centered on a centroid of a region of interest of a tomographic image are added for each rotation angle θ of the radius vector A.

Further, the reference characteristic curve data and the target characteristic curve data may be set as on-circumference pixel value data in which pixel values on the circumference B centered on a centroid of a region of interest of a tomographic image are added for each radius R.

Furthermore, the reference characteristic curve data and the target characteristic curve data may be set as on-ellipse pixel value data in which pixel values on a circumference of an ellipse centered on a centroid of a region of interest of a tomographic image are added for each diameter of the ellipse.

As above, it is possible to specify at least an object part from characteristic curve data indicating a feature of a pixel value distribution of an image such as the on-radius vector pixel value data, the on-circumference pixel value data, or the on-ellipse pixel value data on the basis of a tomographic image, and to perform image processing by selecting an appropriate processing algorithm. Since a processing algorithm appropriate for an image part can be applied, it is possible to perform processing efficiently, and to thereby perform the processing at high speed. In addition, even in a case where an image of the whole body is a processing target, an appropriate processing algorithm can be applied according to a part, and thus image processing can be performed with high efficiency.

In addition, if a processing algorithm is stored in correlation with reference characteristic curve data, for example, for each kind of image such as a presence or absence of a contrast medium in addition to the part, it is possible to apply the optimal processing algorithm according to the kind of image even in the same part. For this reason, it is possible to perform processing at higher speed.

In addition, if parameters used in the processing algorithm are also registered in the algorithm table 2 in correlation with the reference characteristic curve data, a processing can be performed using optimal parameters and processing algorithm for an image, and thus it is possible to perform the processing accurately.

In addition, when position information of a processing target tomographic image is acquired based on a comparison result of the reference characteristic curve data and the target characteristic curve data, and the part presentation image 82 indicating the position information is generated and is displayed, a user can easily confirm a position of the tomographic image, and thus it is possible to provide operation circumstances with high convenience.

Further, the above-described characteristic curve data may be obtained by integrating pixel values (CT values) of a tomographic image, or may be obtained by integrating pixel values ("1" or "0") of a binary image which is obtained by binarizing a tomographic image.

In a case of integrating pixel values of the binary image, an addition processing is easily performed, and thus processing speed increases.

In addition, in a case of integrating pixel values (CT values), a weighting factor depending on the CT values is applied to the CT values which may be added so as to prevent overflow.

In addition, the number of sampling points is preferably normalized in the calculated characteristic curve data. Alternatively, computation is preferably performed by making the number of sampling points equal through interpolation when a degree of correlation is computed. As above, it is possible to accurately obtain a degree of correlation regardless of a physique of an object or the like by making the number of sampling points uniform.

Next, a description will be made of another example of characteristic curve data which is extracted (calculated) from a medical image in the first embodiment.

As shown in FIG. 16, characteristic curve data may be arrangement data in which pixel values on a spiral curve D are sampled centered on a centroid of a region of interest. As shown in FIG. 16(a), CT values may be sampled from a CT image, and, as shown in FIG. 16(b), pixel values ("1" or "0") of a binary image which is binarized may be sampled. An example of the characteristic curve data obtained in FIG. 16(a) is a curve drawn using the transverse axis expressed by a curve length of the spiral curve, and the longitudinal axis expressed by a value which is obtained by multiplying a CT value sampled from the CT image by a weighting factor depending on the CT value. In addition, an example of the characteristic curve data obtained from FIG. 16(b) is a curve drawn using the transverse axis expressed by a curve length of the spiral curve, and the longitudinal axis expressed by a pixel value of 1 or 0.

As in this example, the characteristic curve data in which the pixel values are sampled in a spiral shape is calculated without integrating the pixel values, and thus the characteristic curve data can be extracted at high speed. In addition, if the number of sampling points is to be roughly taken according to the required processing speed, the characteristic curve data can be extracted at higher speed.

In addition, an origin of a radius vector, a circumference, or an ellipse used when calculating the characteristic curve data may be set outside a body.

FIG. 17(a) shows an example in which a radius vector E which has an intersection of a straight line contacting with the object lower side and a straight line contacting with the object left side as an origin is set, and CT values on the radius vector E are integrated for each rotation angle θ from a CT image 30.

In addition, FIG. 17(b) shows an example in which a radius vector E which has an intersection of a straight line contacting with the object lower side and a straight line contacting with the object left side as an origin is set, and binary values on the radius vector E are integrated for each rotation angle θ from a binary image 31.

In addition, FIG. 17(c) shows an example in which a circumference F which has an intersection of a straight line contacting with the object lower side and a straight line contacting with the object left side as an origin is set, and binary values on the circumference F are integrated for each radius Ri from the binary image 31.

As above, any position of an origin of a radius vector, a circumference, and an ellipse for extracting characteristic curve data may be used.

In addition, a shape of a radius vector used when calculating characteristic curve data is not required to be limited to a straight line. For example, if a radius vector of a curve bent according to an organ shape is set, it is possible to obtain characteristic curve data which is more characteristic.

Second Embodiment

Next, the image processing device 100 (the image processing system 1) related to the second embodiment will be described.

A hardware configuration of the image processing device 100 of the second embodiment is the same as that of the image processing device 100 of the first embodiment shown in FIG. 1. The same constituent element as in the image processing device 100 of the first embodiment is given the same reference numeral, and repeated description will be omitted.

In addition, when the CPU 101 of the image processing device 100 of the second embodiment performs intended processing on a processing target image (hereinafter, referred to as a processing image), the CPU executes an algorithm selection processing (refer to FIG. 26) described later so as to select and apply the optimal processing algorithm.

In addition, the storage unit 103 of the image processing device 100 of the second embodiment stores an algorithm table 200 shown in FIG. 18.

In the algorithm table 200 shown in FIG. 18, reference characteristic curve data indicating a feature of a reference image and a processing algorithm according to a processing purpose are stored in correlation with each other for each part. In addition, an anatomical feature of the reference image and a processing algorithm are stored in correlation with each other.

The reference image is an image used to extract a feature or as a reference of comparison among images of each part and each image type. In the algorithm selection processing, described later, an anatomical feature, a characteristic curve (reference characteristic curve data), or the like which is obtained in advance from the reference image is compared with an anatomical feature or a characteristic curve of the processing image, and, as a result, an object part of the processing image or the kind of image is determined.

Figure 19:
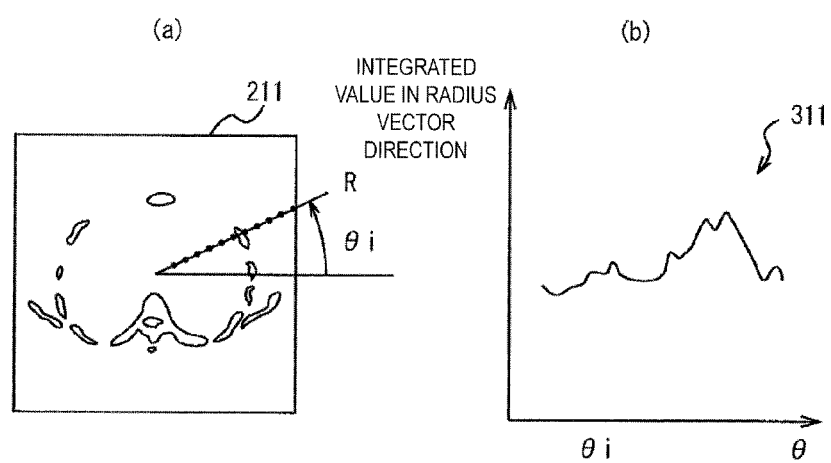
FIG. 19 is a diagram illustrating an example of the reference characteristic curve data (on-radius vector pixel value data 311) calculated from an image 211.
Figure 20:
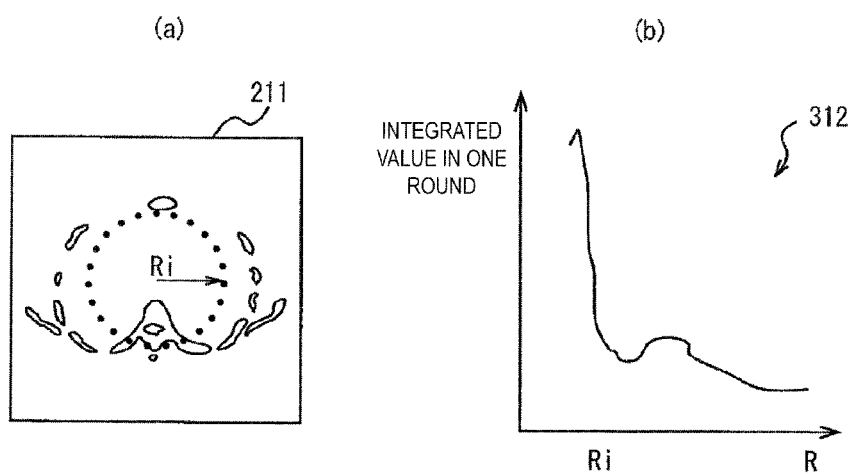
FIG. 20 is a diagram illustrating an example of the reference characteristic curve data (on-circumference pixel value data 312) calculated from the image 211.

As the reference characteristic curve data, the reference characteristic curve data described in the first embodiment may be used. In other words, (1) on-radius vector pixel value data 311 in which pixel values of respective points on a radius vector which rotates centered on a centroid of a region of interest of a reference image 211 are integrated for each rotation angle θ (refer to FIG. 19), and (2) on-circumference pixel value data 312 in which pixel values of respective points on a circumference centered on a centroid of a region of interest of the reference image 211 are integrated for each radius Ri (refer to FIG. 20) may be used.

As described in the first embodiment, (3) on-ellipse pixel value data in which pixel values of respective points on an circumference of an ellipse centered on a centroid of a region of interest are integrated for each diameter Re of the ellipse (either the minor axis or the major axis), (4) on-radius vector pixel value data in which pixel values of respective points on a radius vector which rotates centered on a centroid of a region of interest are multiplied by, for example, a weighting factor corresponding to a distance from the centroid so as to be added with weighting for each rotation angle θ, and (5) on-circumference pixel value data in which pixel values of respective points on a circumference centered on a centroid of a region of interest are multiplied by, for example, a weighting factor corresponding to a rotation angle of the radius vector so as to be added with weighting for each radius Ri, may be used as the above-described reference characteristic curve data.

Figure 21:
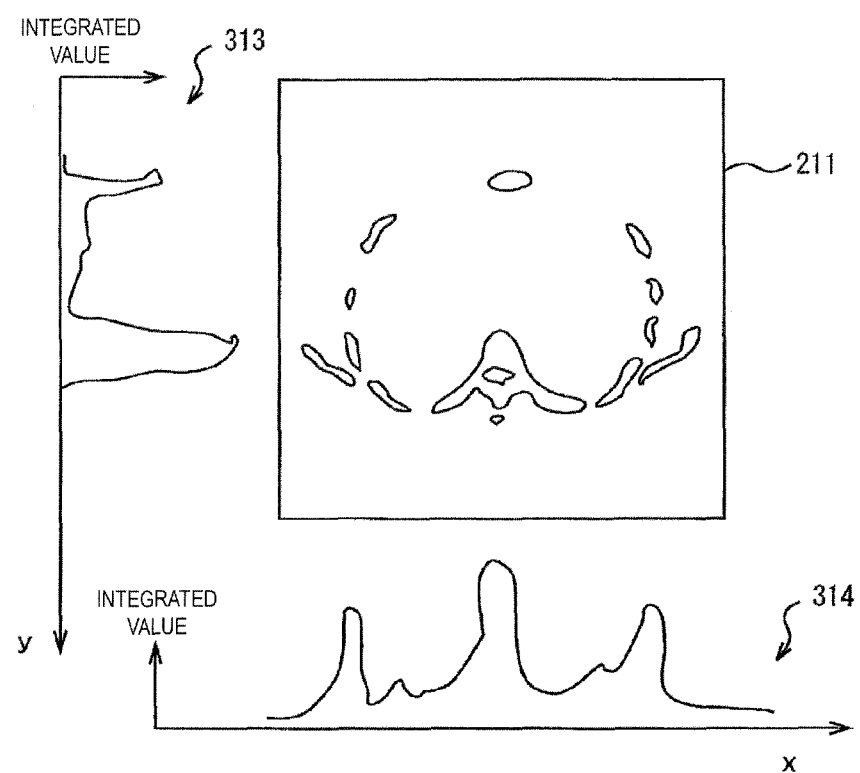
FIG. 21 is a diagram illustrating an example of the reference characteristic curve data (x direction addition data 313, and y direction addition data 314) calculated from the image 211.

In addition, as shown in FIG. 21, a curve (x direction additional data 313) in which pixel values of pixels located in the same line as the x direction of the reference image 211 are added, a curve (y direction additional data 314) in which pixel values of pixels located in the same line as the y direction of the reference image 211 are added, or the like, may be used as the reference characteristic curve data.

Here, the anatomical feature will be described.

The anatomical feature is a feature of an image which is shown for each part in the body axis direction of an object.

The part is, for example, the leg, the abdomen, the chest, the shoulder, the neck, the head, or the like.

Figure 22:
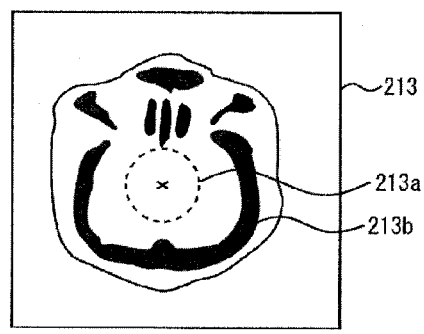
FIG. 22 is a schematic diagram of a cross-sectional view 213 of a top of a head.
Figure 23:
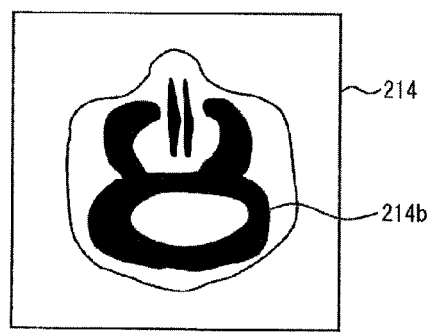
FIG. 23 is a schematic diagram of a cross-sectional view 214 of a vicinity of eyeballs of the head.

From a density distribution of the image, it is possible to recognize an arrangement of the bones, a ratio of the bones to the object, or presence of an air region. For example, images 213 and 214 shown in FIGS. 22 and 23 are images of the brain, the reference numerals 213b and 214b indicate the bone region, but there is an anatomical feature in which there is no bone around the center of the brain 213a (however, there is a case where a certain number of calcified regions are found). In other words, generally, it is possible to determine whether or not an image is a brain image from a ratio of high density regions present around the object center.

However, there are cases where, in the head, algorithms applied to an image processing are preferably changed in the top as shown in the image 213 of FIG. 22 and the vicinity of the eyeball as shown in the image 214 of FIG. 23.

Therefore, even in an image indicating the anatomical feature of the head, a part is further subdivided, and different processing algorithms are required to be applied for each part.

Figure 24:
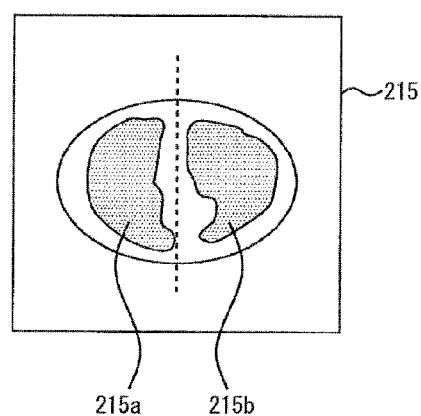
FIG. 24 is a schematic diagram of a cross-sectional view 215 of a chest.

In addition, FIG. 24 is an image 215 illustrating a lung field.

As shown in FIG. 24, the lung field has an anatomical feature in which there are air regions 215a and 215b of which a CT value (pixel value) is small and the area is considerably large inside the object.

Figure 25:
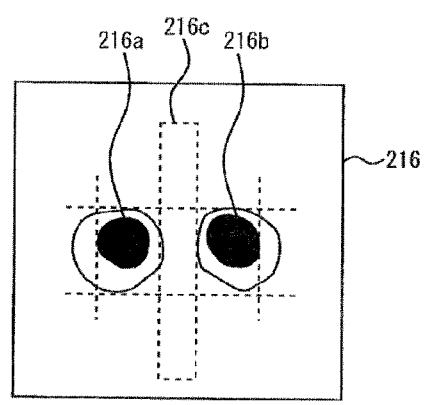
FIG. 25 is a schematic diagram of a cross-sectional view 216 of legs.

Further, FIG. 25 shows an image 216 indicating the legs.

As shown in FIG. 25, the legs have an anatomical feature in which there are two bone regions 216a and 216b which have the approximately same area in the left and right and a region 216c where there is no bone between the left and right bone regions.

As above, there is a case where a part can be immediately determined from the anatomical feature and thus a processing algorithm to be applied can be decided in a one-to-one relationship.

In addition, there is a case where a different processing algorithm is required to be applied when image processing is performed, according to a further subdivided part or the kind of image depending on a part.

In addition, there is a case where an anatomical feature cannot be found from an image.

In the second embodiment, before selecting a processing algorithm using a characteristic curve, first, in relation to an image of a specific part in which a processing algorithm may not be changed due to a subdivided part or kind of image, a processing algorithm to be applied is decided in a one-to-one relationship from an anatomical feature thereof. In addition, in relation to an image of a specific part in which a processing algorithm is required to be changed due to a subdivided part or kind of image, a characteristic curve is calculated, correlation between the calculated characteristic curve and a plurality of specific reference characteristic curve data items decided from an anatomical feature is determined, and a processing algorithm to be applied is decided based on a result thereof. Further, in relation to an image in which an anatomical feature is not correlated with a processing algorithm, correlation between a characteristic curve calculated from the image and reference characteristic curve data is determined, and a processing algorithm to be applied is decided based on a result thereof.

The algorithm table 200 of the second embodiment will be described with reference to FIG. 18.

The algorithm table 200 stores algorithms A21, A22, A23, . . . in which the algorithms and the anatomical features are correlated with each other in a one-to-one relationship, and algorithms An_01, An_02, An_03, . . . in which the algorithms and the anatomical features are correlated with each other in a one-to-many (group) relationship, and other algorithms (not correlated with anatomical features) Am, Am+1, . . . .

For example, the algorithms A21, A22, A23, are correlated with anatomical features C21, C22, C23, . . . in a one-to-one relationship. In an algorithm selection processing (refer to FIG. 26) described later, in a case where an anatomical feature extracted from a processing image is correlated with an algorithm in a one-to-one relationship, the correlated processing algorithm is immediately selected and is applied to an image processing.

In addition, the algorithms An_01, An_02, An_03, An_04, An+1_01, An+1_02, . . . are correlated with the anatomical features in a one-to-many relationship. In a part (the chest in the example of FIG. 18) showing the anatomical feature Cn, algorithms to be applied are different in the upper part and the lower part of a body axis direction, and further, algorithms to be applied are different depending on a presence or absence of a contrast medium. For this reason, the characteristic curves shown in FIGS. 19 to 21 and the like are used to determine a more accurate part or a presence or absence of a contrast medium from a feature of an image. The reference characteristic curve data and the algorithm are correlated with each other in a one-to-one relationship. In the algorithm selection processing described later, in a case where the anatomical feature Cn extracted from a processing image is correlated with an algorithm in a one-to-many relationship, correlation between a plurality of reference characteristic curve data items D21 to D24 correlated with the anatomical feature Cn and a characteristic curve calculated from the processing image is determined so as to decide reference characteristic curve data with a high degree of correlation, and an algorithm correlated with the reference characteristic curve data is selected and is applied.

In addition, the algorithms Am, Am+1, . . . are not correlated with any anatomical feature. However, the algorithms Am, Am+1, . . . are correlated with the reference characteristic curve data items Dm, Dm+1, . . . in a one-to-one relationship.

In the algorithm selection processing, described later, in a case where a specific anatomical feature cannot be extracted from a processing image, correlation between a characteristic curve calculated from the processing image and the reference characteristic curve data items Dm, Dm+1, . . . which are not correlated with any anatomical feature is determined so as to decide reference characteristic curve data with a high degree of correlation, and an algorithm correlated with the reference characteristic curve data is selected and is applied.

Next, with reference to FIG. 26, an operation of the image processing device 100 of the second embodiment will be described.

Figure 26:
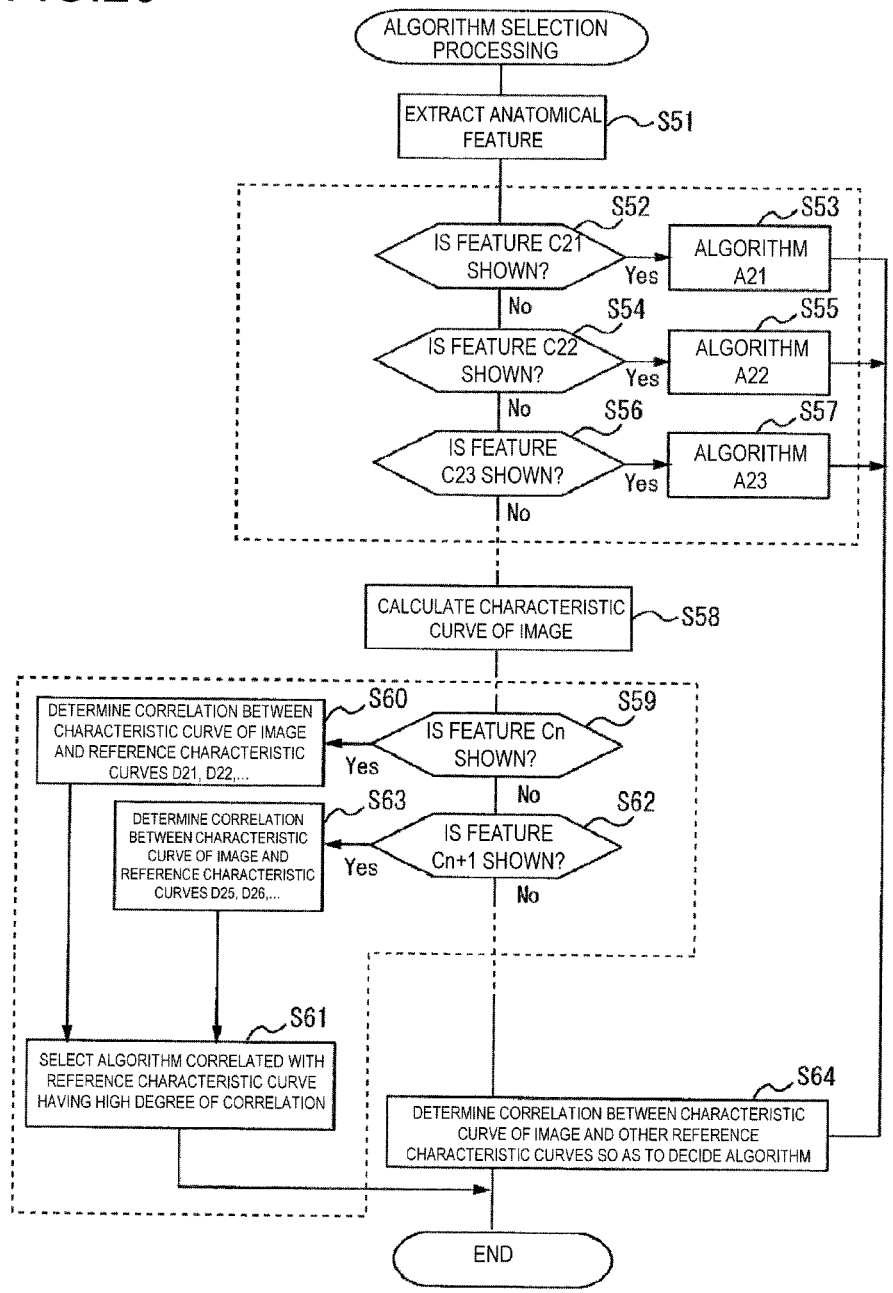
FIG. 26 is a flowchart illustrating a flow of an algorithm selection processing of the second embodiment.

The CPU 101 of the image processing device 100 reads from the main memory 102 a program and data regarding the algorithm selection processing shown in FIG. 26 and executes the processing on the basis of the program and data.

The CPU 101 of the image processing device 100 first acquires an image (CT image) which is a processing target, and obtains an anatomical feature from the acquired image (step S51).

Next, the CPU 101 determines whether or not the anatomical feature obtained in step S51 is a specific anatomical feature which is correlated with an algorithm in a one-to-one relationship. In other words, if the anatomical feature obtained in step S51 is the feature C21 (step S52; Yes), the algorithm A21 correlated with the anatomical feature C21 in a one-to-one relationship is selected from the algorithm table 200 (step S53). In addition, if the anatomical feature obtained in step S51 is the feature C22 (step S54; Yes), the algorithm A22 correlated with the anatomical feature C22 in a one-to-one relationship is selected from the algorithm table 200 (step S55), and, if the anatomical feature obtained in step S51 is the feature C23 (step S56), the algorithm A23 correlated with the anatomical feature C23 in a one-to-one relationship is selected from the algorithm table 200 (step S57).

As above, first, if there is an anatomical feature correlated with an algorithm in a one-to-one relationship, the algorithm is immediately selected based on the anatomical feature.

If the anatomical feature obtained in step S51 does not match the specific anatomical feature correlated with in a one-to-one relationship (No in steps S52, S53 and S54), next, the CPU 101 calculates a predetermined characteristic curve for the processing image (step S58). Hereinafter, the characteristic curve data calculated for the processing target image is referred to as target characteristic curve data. The target characteristic curve data calculated here is assumed to be characteristic curve data of the same kind as the reference characteristic curve data stored in the algorithm table 200. For example, in a case where the reference characteristic curve data stored in the algorithm table 200 is the on-radius vector pixel value data 311 as shown in FIG. 19(b), the same on-radius vector pixel value data 311 may also be obtained in step S58.

If the anatomical feature calculated in step S51 is correlated with algorithms in a one-to-many (group) relationship (in other words, different algorithms are required to be applied depending on a subdivided part or kind of image), first, the CPU 101 determines what kind of anatomical feature is shown, and further determines correlation between the target characteristic curve data calculated in step S58 and the reference characteristic curve data in the group correlated with the corresponding anatomical feature so as to select an algorithm.

In other words, if the anatomical feature of the processing image calculated in step S51 is the feature Cn (step S59; Yes), correlation between a plurality of reference characteristic curve data items D21 to D24 correlated with the anatomical feature Cn and the target characteristic curve data calculated in step S58 is determined (step S60). In addition, an algorithm correlated with reference characteristic curve data having a high degree of correlation is selected from the algorithm table 200 (step S61).

Similarly, if the anatomical feature of the processing image calculated in step S51 is the feature Cn+1 (step S62; Yes), correlation between a plurality of reference characteristic curve data items D25 and D26 correlated with the anatomical feature Cn+1 and the target characteristic curve data calculated in step S58 is determined (step S63). In addition, an algorithm correlated with reference characteristic curve data having a high degree of correlation is selected from the algorithm table 200 (step S61).

If the anatomical feature obtained in step S51 is not correlated with any algorithm (step S62; No), the CPU 101 refers to the algorithm table 200, determines correlation between the other reference characteristic curve data items Dm, Dm+1, . . . (not correlated with any anatomical feature) and the target characteristic curve data calculated in step S58, and selects an algorithm correlated with reference characteristic curve data having a high degree of correlation from the algorithm table 200 (step S64).

In this way, the processing algorithm to be applied to the image is selected.

In addition, in the above-described processing procedures, the processings in steps S59 to S62 may not be necessarily provided; and, after an algorithm is selected using an anatomical feature in a one-to-one relationship (steps S51 to S57), a characteristic curve of a processing image may be calculated, and correlation between the target characteristic curve data and reference characteristic curve data in the algorithm table 200 may be determined so as to decide an algorithm.

As described above, the image processing device 100 of the second embodiment includes the algorithm table 200 which stores an anatomical feature of a reference image or reference characteristic curve data and a processing algorithm in correlation with each other. In addition, in the algorithm selection processing, first, the CPU 101 extracts an anatomical feature from a processing image, and selects from the algorithm table 200 a processing algorithm which is correlated with the extracted anatomical feature in a one-to-one relationship. In a case where the extracted anatomical feature is not correlated with a processing algorithm in a one-to-one relationship, a characteristic curve indicating a feature of the image is extracted from the processing image, reference characteristic curve data having high correlation with the calculated characteristic curve is decided, and a processing algorithm correlated with the decided reference characteristic curve data is selected from the algorithm table 200.

Therefore, in a case where a processing algorithm to be applied can be immediately decided from an anatomical feature, a processing such as calculation of a characteristic curve of the processing image or determination of correlation between target characteristic curve data and reference characteristic curve data can be omitted, and thus computation can be performed at high speed.

Further, in a case where a part specified from an anatomical feature is subdivided into a plurality of parts or is subdivided into a plurality of kinds of images, the reference characteristic curve data items are grouped for each subdivided part or each kind of image and are stored in the algorithm table 200 in correlation with a corresponding anatomical feature. In the algorithm selection processing, in a case where an anatomical feature extracted from the processing image is not correlated with a processing algorithm in a one-to-one relationship, first, a plurality of reference characteristic curve data items included in a group corresponding to the anatomical feature are read from the algorithm table 200, reference characteristic curve data having high correlation with the characteristic curve is decided among a plurality of read reference characteristic curve data items, and a processing algorithm correlated with the decided reference characteristic curve data is selected from the algorithm table 200.

Since a plurality of reference characteristic curve data items included in a group corresponding to an anatomical feature are defined in advance in the algorithm table 200, a reference characteristic curve for performing correlation determination can be restricted, and thus it is possible to omit a wasteful correlation determination processing and to thereby perform computation at higher speed.

As above, although the preferred embodiments of the image processing device related to the present invention have been described with reference to the accompanying drawings, the present invention is not limited to these examples. It is obvious that a person skilled in the art can conceive of a variety of modifications or alterations within the scope of the technical spirit disclosed in the present application, and it is understood that they are also naturally included in the technical scope of the present invention.

REFERENCE SIGNS LIST

1 Image processing system, 100 Image processing device, 101 CPU, 102 Main memory, 103 Storage unit, 104 Communication I/F, 105 Display memory, 106 I/F, 107 Display unit, 108 Mouse, 109 Input unit, 2 Algorithm table, 30 Chest tomographic image (without contrast medium), 40 Chest tomographic image (presence of contrast medium), 50 Upper chest end tomographic image (without contrast medium), 60 Abdomen tomographic image (with contrast medium), 3A, 4A, 5A and 6A On-radius vector pixel value data, 3B, 4B, 5B and 6B On-circumference pixel value data, 82 Part presentation image, 91 MIP image before rib removal processing is performed, configured from chest image with contrast medium, 92 MIP image after rib removal processing is performed, configured from chest image with contrast medium, 93 MIP image after rib removal processing is performed, configured from chest image without contrast medium, A Radius vector for extracting characteristic curve data, B Circumference for extracting characteristic curve data, C Curve (spiral shape) for extracting characteristic curve data, E Radius vector for extracting characteristic curve data (origin is located outside body), F Circumference for extracting characteristic curve data (origin is located outside body), 200 Algorithm table, 211 to 215 Image, 311 On-radius vector pixel value data, 312 On-circumference pixel value data, 313 x direction additional data, 314 y direction additional data

The invention claimed is:

1. An image processing device which applies a predetermined processing algorithm to a medical image so as to perform an image processing, comprising:
 a storage unit that calculates reference characteristic curve data in which pixel values are computed centered on any point of a region of interest for a reference image, and stores the reference characteristic curve data and a part in correlation with each other in advance;
 a calculation unit that calculates target characteristic curve data in which pixel values are computed centered on any point of a region of interest for a processing target image;
 a comparison unit that compares the target characteristic curve data calculated by the calculation unit with the reference characteristic curve data stored in the storage unit;
 a selection unit that selects a part stored in correlation with reference characteristic curve data having high correlation with the target characteristic curve data from the storage unit on the basis of a result of the comparison by the comparison unit; and
 an image processing unit that performs image processing to which a processing algorithm corresponding to the part selected by the selection unit is applied.

2. The image processing device according to claim 1, wherein the reference characteristic curve data and the target characteristic curve data are on-radius vector pixel value data in which pixel values on a radius vector centered on a centroid of a region of interest of the image are added for each rotation angle.

3. The image processing device according to claim 1, wherein the reference characteristic curve data and the target characteristic curve data are on-circumference pixel value data in which pixel values on a circumference centered on a centroid of a region of interest of the image are added for each radius.

4. The image processing device according to claim 1, wherein the reference characteristic curve data and the target characteristic curve data are on-ellipse pixel value data in which pixel values on a circumference of an ellipse centered on a centroid of a region of interest of the image are added for each diameter of the ellipse.

5. The image processing device according to claim 1, wherein the reference characteristic curve data is acquired depending on presence or absence of a contrast medium, and is stored in the storage unit in correlation with a processing algorithm for each part and each kind of image.

6. The image processing device according to claim 1, wherein the storage unit further stores a parameter used in the processing algorithm in correlation with the reference characteristic curve data.

7. The image processing device according to claim 1, further comprising:
 a display unit that acquires position information of the processing target image on the basis of the comparison result by the comparison unit, and displays a part presentation image indicating the position information.

8. The image processing device according to claim 1, wherein the comparison unit compares target characteristic curve data with reference characteristic curve data for a series of images of cross-section positions including a target image.

9. The image processing device according to claim 1, wherein the comparison unit obtains the correlation on the basis of an inter-curve distance between the reference characteristic curve data and the target characteristic curve data.

10. The image processing device according to claim 1, wherein the reference characteristic curve data and the target characteristic curve data are calculated by adding pixel values of the target image with weighting or by integrating pixel values of a binary image which is obtained by binarizing the image.

11. The image processing device according to claim 1, wherein the storage unit further stores an anatomical feature of the reference image and the processing algorithm in correlation with each other, and
 wherein the selection unit extracts the anatomical feature from the processing target image before performing selection based on the comparison result, and selects the processing algorithm which is correlated with the extracted anatomical feature in a one-to-one relationship from the storage unit.

12. The image processing device according to claim 11, wherein, when a part specified from the anatomical feature is further subdivided into a plurality of parts or a plurality of kinds of images, the storage unit groups the reference characteristic curve data items for each subdivided part or each kind of image so as to be stored in correlation with the corresponding anatomical feature, and
 wherein, when the processing algorithm is not correlated with the anatomical feature extracted from the processing target image in a one-to-one relationship, first, the selection unit reads a plurality of reference characteristic curve data items included in a group corresponding to the anatomical feature from the storage unit, decides the reference characteristic curve data having high correlation with the target characteristic curve data among the plurality of read reference characteristic curve data items, and selects the processing algorithm correlated with the decided reference characteristic curve data from the storage unit.

13. The image processing device according to claim 11, wherein the anatomical feature is any one of a ratio of bone regions present around an object center, a ratio of a lung field region to the area of the object, and presence of two bone regions and presence of a region where there is no bone between the two bone regions.

14. An image processing method of applying a predetermined processing algorithm to a medical image so as to perform an image processing, comprising:
- a storage step of calculating reference characteristic curve data in which pixel values are computed centered on any point of a region of interest for a reference image, and storing the reference characteristic curve data and a part in correlation with each other in advance;
- a calculation step of calculating target characteristic curve data in which pixel values are computed centered on any point of a region of interest for a processing target image;
- a comparison step of comparing the target characteristic curve data calculated in the calculation step with the reference characteristic curve data stored in the storage step;
- a selection step of selecting a processing algorithm stored in correlation with reference characteristic curve data having high correlation with the target characteristic curve data from the storage step on the basis of a result of the comparison in the comparison step; and
- an image processing step of performing an image processing to which a processing algorithm corresponding to the part selected in the selection step is applied.

* * * * *